(12) United States Patent
Di Pardo et al.

(10) Patent No.: US 10,869,632 B2
(45) Date of Patent: Dec. 22, 2020

(54) SYSTEM AND METHOD FOR ERGONOMIC ANALYSIS, IN PARTICULAR OF A WORKER

(71) Applicant: C.R.F. Società Consortile per Azioni, Orbassano (IT)

(72) Inventors: Massimo Di Pardo, Orbassano (IT); Giorgio Pasquettaz, Orbassano (IT); Rossella Monferino, Orbassano (IT); Francesca Gallo, Orbassano (IT)

(73) Assignee: C.R.F. Società Consortile per Azioni, Orbassano (IT)

( * ) Notice: Subject to any disclaimer, the term of this patent is extended or adjusted under 35 U.S.C. 154(b) by 163 days.

(21) Appl. No.: 16/254,708

(22) Filed: Jan. 23, 2019

(65) Prior Publication Data

US 2019/0290202 A1 Sep. 26, 2019

(30) Foreign Application Priority Data

Jan. 24, 2018 (EP) .................................. 18153311

(51) Int. Cl.
*A61B 5/00* (2006.01)
*A41D 19/00* (2006.01)
(Continued)

(52) U.S. Cl.
CPC .......... *A61B 5/6806* (2013.01); *A41D 19/001* (2013.01); *A41D 19/0027* (2013.01);
(Continued)

(58) Field of Classification Search
CPC .......... A61B 2562/04; A61B 2562/066; A61B 2562/0219; A61B 2562/0247;
(Continued)

(56) References Cited

U.S. PATENT DOCUMENTS 9,971,404 B2 * 5/2018 Messingher .......... A63F 13/212
9,996,153 B1 * 6/2018 Trotta ..................... G06F 3/016
(Continued)

FOREIGN PATENT DOCUMENTS

WO WO-2012018543 A2 * 2/2012 ............. A61B 5/224
WO WO-2018016192 A1 * 1/2018 ............. G06T 19/00

OTHER PUBLICATIONS

European Search Report dated Jul. 6, 2018 (8 pages).

*Primary Examiner* — Jonathan M Dunlap
(74) *Attorney, Agent, or Firm* — RMCK Law Group, PLC

(57) ABSTRACT

Described herein is a system and method for ergonomic analysis including a sensorized glove having an inner glove including a plurality of extensometer sensors for detecting relative movements between parts of a worker's hand, and an outer glove including a plurality of pressure sensors distributed over a palmar surface and for detecting pressure exerted in corresponding areas of said palmar surface; a wearable network of sensors being located in the network so that they can be associated to corresponding joints of the human body; a unit for generating a sequence of images of a worker task; and a processing unit for receiving data and/or signals from the sensorized glove, from the wearable sensor network, and/or from the unit, and configured for processing said data and/or signals to estimate ergonomic indicators and/or to obtain local information of effort and/or posture.

15 Claims, 23 Drawing Sheets

(51) Int. Cl.

| | | |
|---|---|---|
| *A61B 5/11* | (2006.01) | |
| *G06F 3/01* | (2006.01) | |
| *G06T 11/60* | (2006.01) | |
| *G16H 20/30* | (2018.01) | |
| *A61B 5/22* | (2006.01) | |
| *G16H 40/63* | (2018.01) | |
| *G06Q 10/06* | (2012.01) | |
| *H04L 29/08* | (2006.01) | |
| *A61B 5/107* | (2006.01) | |

(52) U.S. Cl.
CPC .......... *A61B 5/0024* (2013.01); *A61B 5/0077* (2013.01); *A61B 5/1116* (2013.01); *A61B 5/1122* (2013.01); *A61B 5/1125* (2013.01); *A61B 5/1128* (2013.01); *A61B 5/22* (2013.01); *A61B 5/225* (2013.01); *A61B 5/4561* (2013.01); *G06F 3/014* (2013.01); *G06F 3/017* (2013.01); *G06Q 10/06398* (2013.01); *G06T 11/60* (2013.01); *G16H 20/30* (2018.01); *G16H 40/63* (2018.01); *A41D 2600/20* (2013.01); *A61B 5/1071* (2013.01); *A61B 2503/20* (2013.01); *A61B 2562/0219* (2013.01); *A61B 2562/0247* (2013.01); *A61B 2562/04* (2013.01); *A61B 2562/066* (2013.01); *H04L 67/12* (2013.01)

(58) Field of Classification Search
CPC ..... A61B 5/077; A61B 5/0024; A61B 5/1071; A61B 5/1116; A61B 5/1122; A61B 5/1125; A61B 5/1128; A61B 5/22; A61B 5/225; A61B 5/4561; A61B 5/6806; A41D 19/001; A41D 19/0027; A41D 2600/20; G06Q 10/06398; G06F 3/014; G06F 3/017; G06T 11/60; H04L 67/12; G16H 20/30; G16J 40/63

See application file for complete search history.

(56) References Cited

U.S. PATENT DOCUMENTS

| | | | |
|---|---|---|---|
| 10,055,018 B2 * | 8/2018 | Tokubo | G02B 27/0093 |
| 10,321,873 B2 * | 6/2019 | Connor | A61B 5/01 |
| 2005/0151722 A1 * | 7/2005 | Meteyer | G06F 3/011 |
| | | | 345/158 |
| 2011/0234483 A1 * | 9/2011 | Lan | A63F 13/235 |
| | | | 345/156 |
| 2013/0197399 A1 * | 8/2013 | Montgomery | A61B 5/1125 |
| | | | 600/595 |
| 2015/0320127 A1 * | 11/2015 | Wegner | A41D 19/01558 |
| | | | 2/20 |
| 2016/0054797 A1 * | 2/2016 | Tokubo | G06F 3/016 |
| | | | 345/633 |
| 2016/0070958 A1 * | 3/2016 | Whelan | A61B 5/1123 |
| | | | 382/107 |
| 2016/0174897 A1 * | 6/2016 | Sherman | A61B 5/6806 |
| | | | 600/476 |
| 2016/0259408 A1 | 9/2016 | Messingher et al. | |
| 2016/0338644 A1 | 11/2016 | Connor | |
| 2017/0076495 A1 * | 3/2017 | Gabrys | G06F 30/00 |
| 2017/0303853 A1 * | 10/2017 | McMillen | G01L 1/2206 |
| 2018/0196515 A1 * | 7/2018 | Appleyard | G06F 3/016 |
| 2019/0012837 A1 * | 1/2019 | Myers | G02B 27/01 |
| 2019/0290202 A1 * | 9/2019 | Di Pardo | G06F 3/014 |
| 2020/0121479 A1 * | 4/2020 | Thompson | A41D 19/0006 |

* cited by examiner

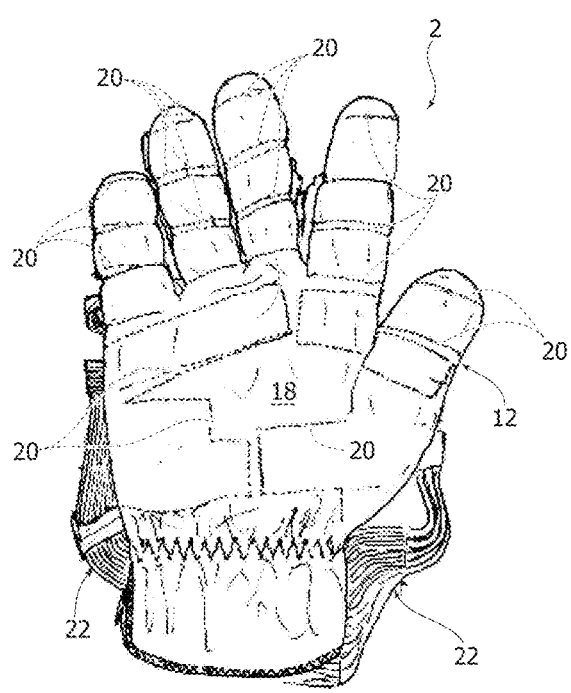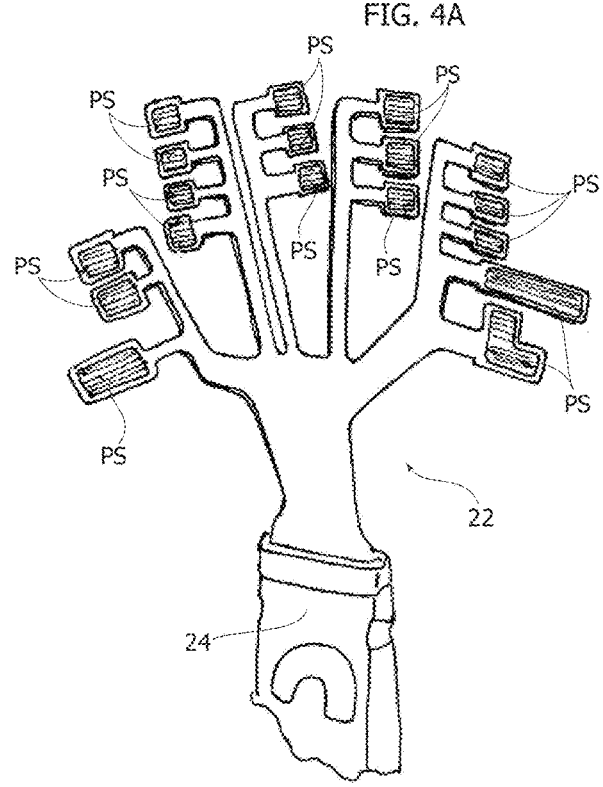

FIG. 9A
FIG. 9B
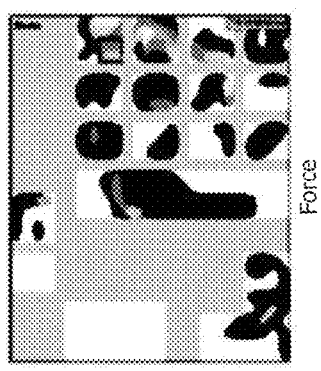
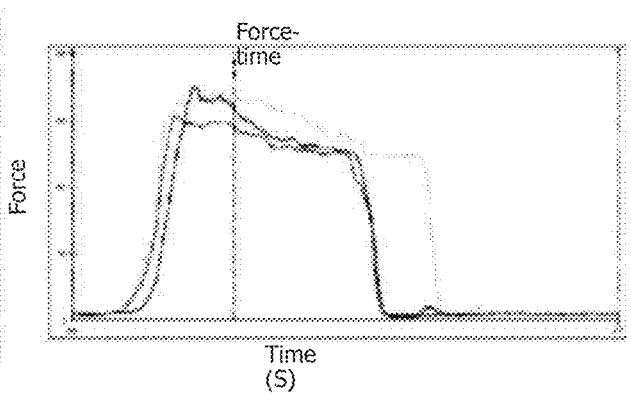

FIG. 9C

FIG. 10A
FIG. 10B
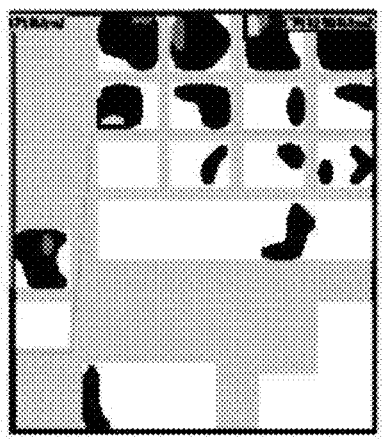
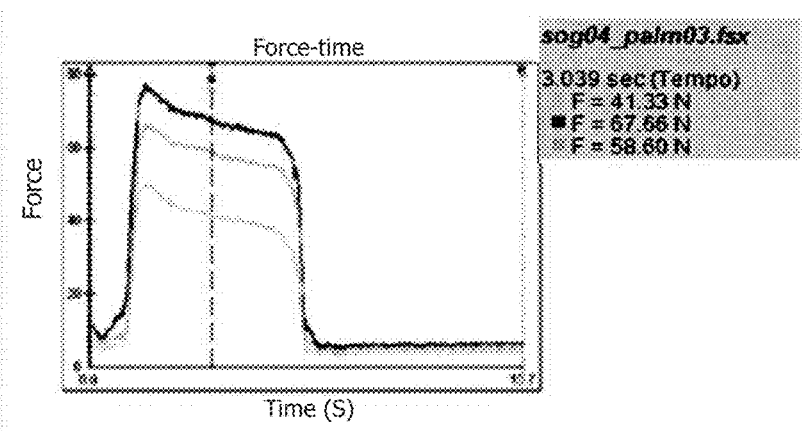

FIG. 11A
FIG. 11B
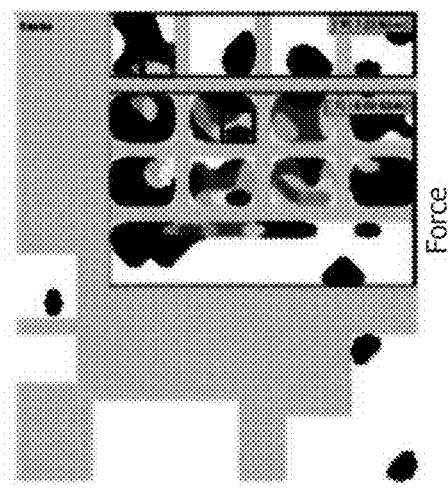
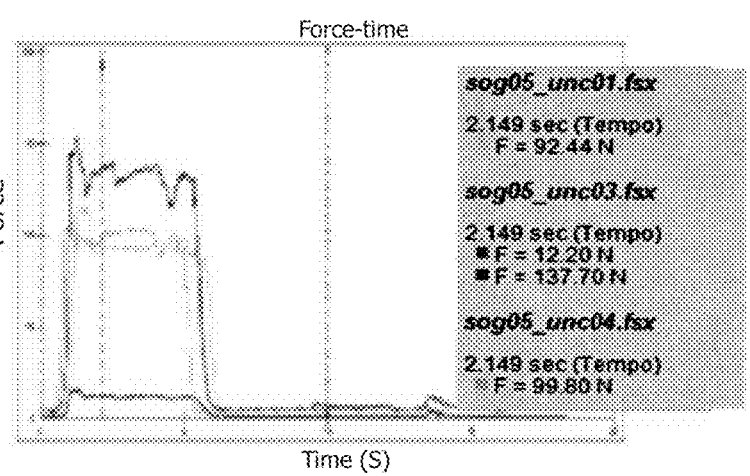

FIG. 12A
FIG. 12B
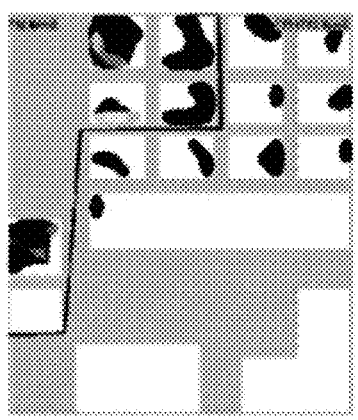
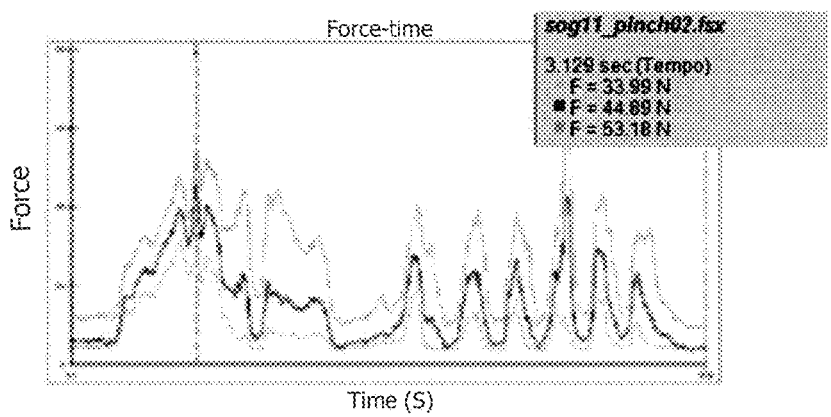

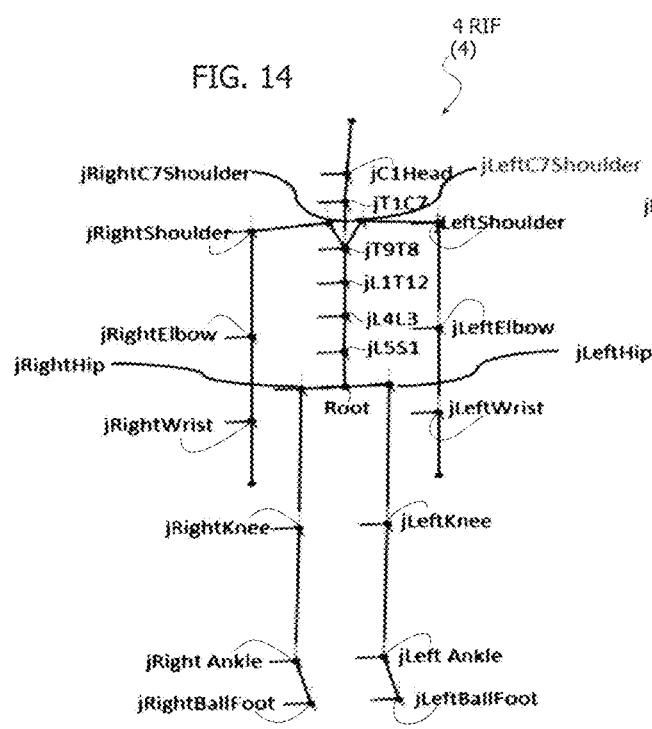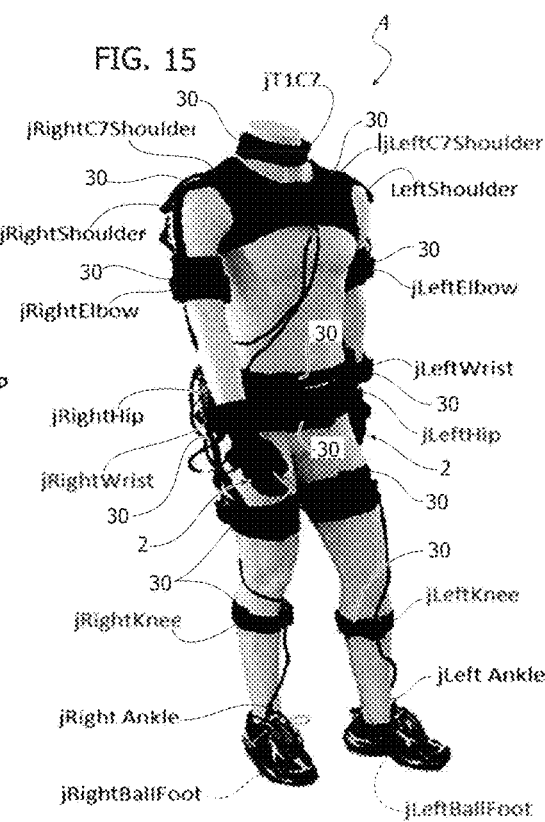

FIG. 17
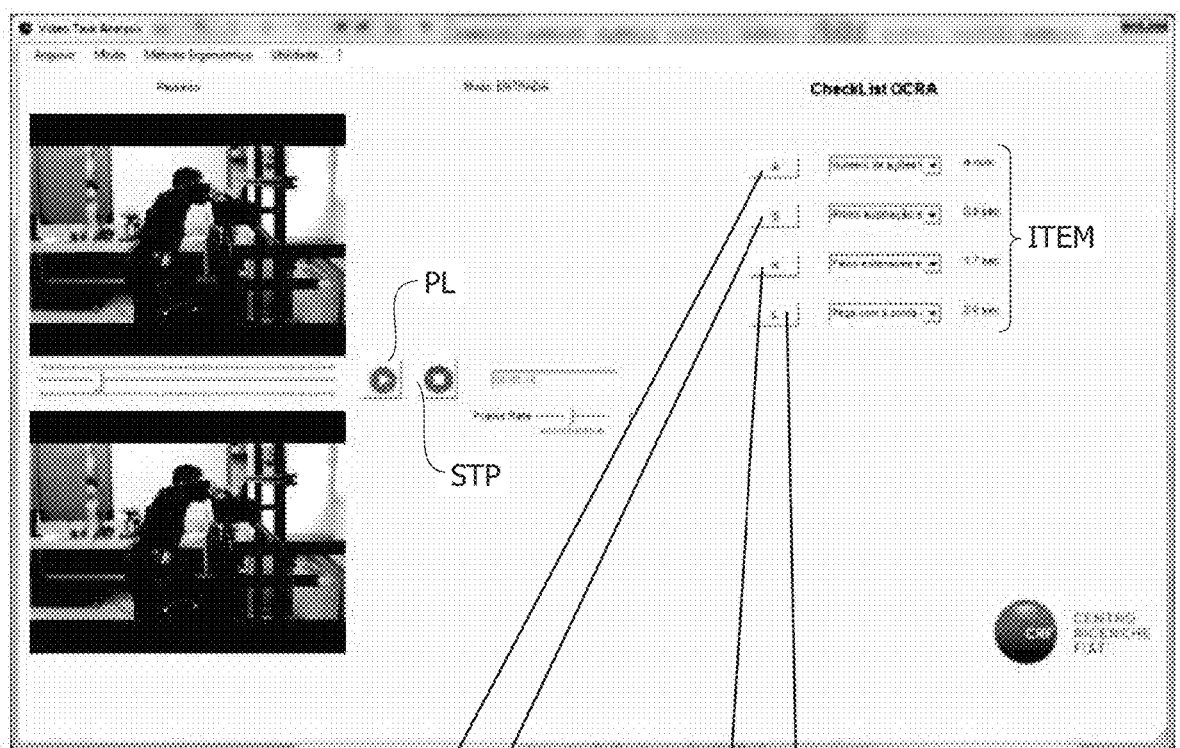
A.
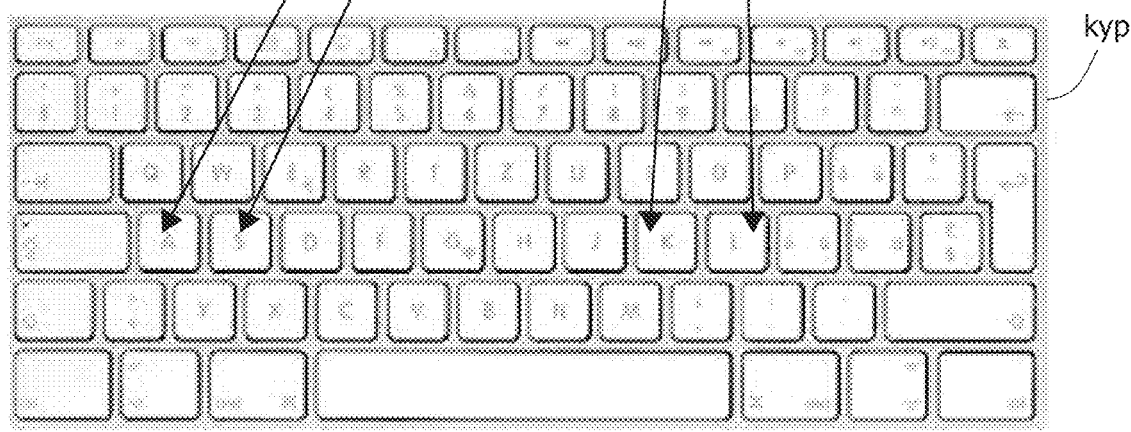
B.

FIG. 20
A.
B.
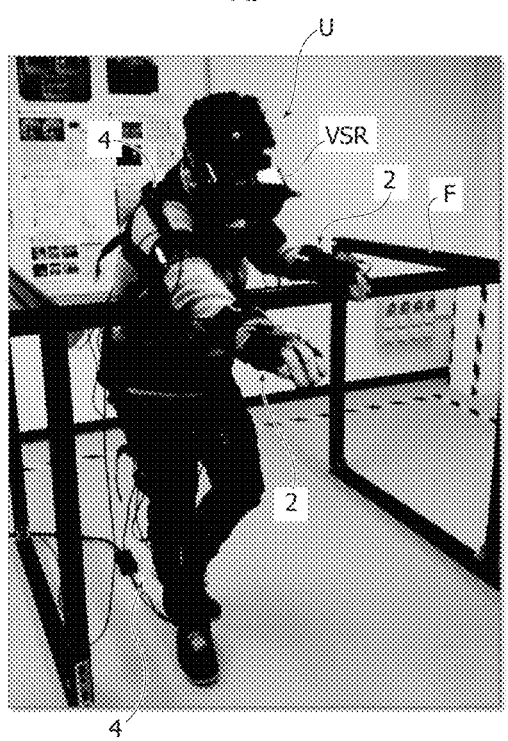
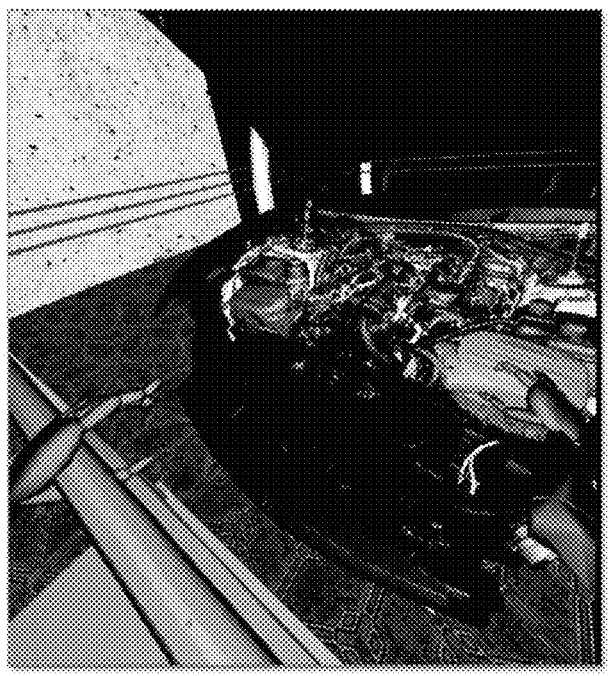

FIG. 21
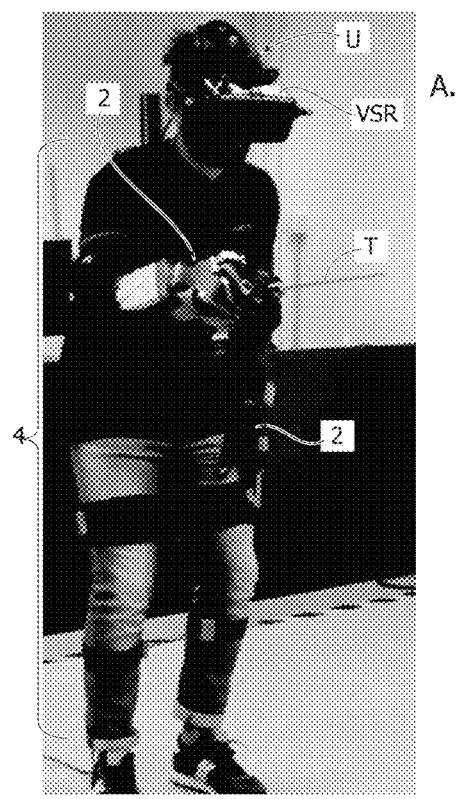
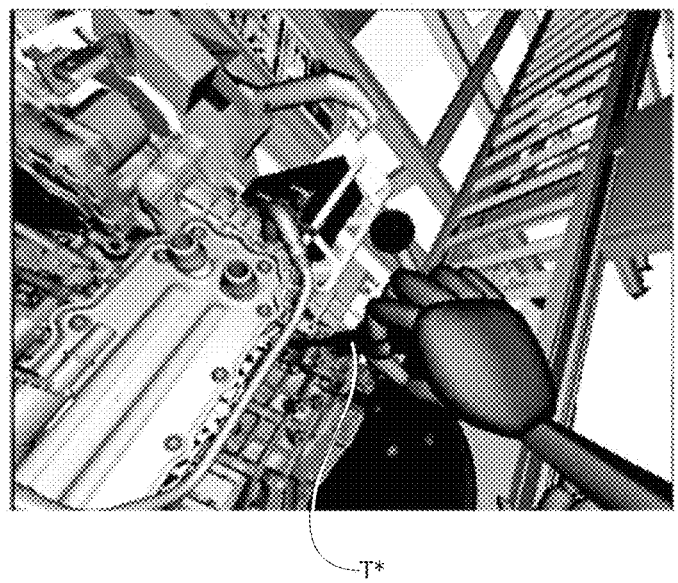

SYSTEM AND METHOD FOR ERGONOMIC ANALYSIS, IN PARTICULAR OF A WORKER

CROSS-REFERENCE TO RELATED APPLICATION

This application claims priority to European Patent Application No. 18153311.8 filed Jan. 24, 2018. The disclosure of the above application is incorporated herein by reference in its entirety.

FIELD OF THE INVENTION

The present invention relates to systems for ergonomic analysis of a subject, in particular a worker, and more in particular to systems applied to the analysis of movements, actions, and posture of a line operator responsible for vehicle assembly.

Prior Art and General Technical Problem

In the manufacturing and metal-engineering industry, workers are called upon to carry out sequenced and repetitive operations, for which it is necessary to guarantee a minimum level of ergonomic compatibility with humans in order to prevent risks to health and physical integrity of operators.

In this context, the metal-engineering industry, and in particular the automotive industry, are characterized by a plurality of tasks that are very different from one another and are carried out innumerable times during the day, with times dictated by the production needs. It thus becomes crucial to perform a careful ergonomic assessment of these actions in order to make—if and where required postural corrections, and/or corrections of movement and/or of action.

The ergonomic analysis that can be carried out using the systems and methods based upon the prior art in general exploits the following techniques:
  visual analysis of the worker performed by an operator responsible for ergonomic monitoring; this process is based upon acquisition of images of the worker at work and upon subsequent analysis by the operator; the process is to a large extent carried out manually/empirically, and is thereby afflicted by a subjective variability, which, albeit controllable, cannot be eliminated altogether; it is moreover rather demanding in terms of temporal resources; and
  acquisition of the positions of parts of the body and/or of the long bones via images and video clips and processing of the data thus obtained; even though this methodology is practically free from subjective variability, it is markedly penalised by the fact that only part of the human body is covered and/or by the fact that the reading resolution (for ergonomic purposes) is too low; this means that the methodology is a long way from meeting the needs linked to estimating the main ergonomic indicators.

Finally, and in part as a consequence of the foregoing, with the systems and methods currently known any activity of ergonomic analysis performed on the worker's hand is substantially impracticable, and even less is it possible to implement this analysis in real time and with objective means not linked to the subjectivity of the operator responsible for ergonomic monitoring.

OBJECT OF THE INVENTION

The object of the present invention is to solve the technical problem mentioned previously.

In particular, an object of the invention comprises providing a methodological supporting tool for ergonomic analysis in the stage of observation and design that will at the same time be objective and fast to implement. Particular reference will be made to the development of a methodology of analysis of the activities performed by a worker at a workstation, deriving, from this analysis, factors that are useful for improving in the design stage the product/process parameters on the assembly lines and/or optimising the characteristics of the workstation.

Moreover, an object of the present invention may be to provide a single interface for collection of ergonomic data from a plurality of devices forming part of the system, for example displays, devices for capturing the movement of the body, and/or devices for capturing the movement and force of the hands (for example, accelerometers, pressure sensors, etc.).

Further objects of the invention comprise:
  identifying critical actions during a working activity; and/or
  identifying the main aspects that are critical from an ergonomic standpoint; and/or
  providing an ergonomic assessment in compliance with company and international standards; and/or
  providing a system and a method for collection of postural and dynamic data with high repeatability, and for subsequent analysis thereof applied to a worker's hand.

SUMMARY OF THE INVENTION

The object of the invention is achieved by a system and a method having the characteristics that form the subject of the ensuing claims, which constitute an integral part of the technical teaching provided herein in relation to the invention.

BRIEF DESCRIPTION OF THE DRAWINGS

The invention will now be described with reference to the annexed drawings, which are provided purely by way of non-limiting example and in which:
FIG. 2A illustrates a position of calibration of the device of FIG. 2;
FIG. 4 is a view according to the arrow IV of FIG. 2;
FIG. 4A is an example of a sensor network;
FIGS. 9A to 12C illustrate results provided by way of example that can be obtained during operation of the device of FIG. 2.

FIG. 14 is a schematic representation of a further element of the system according to the invention;

FIG. 15 illustrates a preferred embodiment of the element represented schematically in FIG. 14;

FIGS. 16 to 19 illustrate some interface screens of a software for management of the system according to the invention; and FIGS. 20 and 21, each including a portion "A" and a portion "B", illustrate a mode of acquisition of a sequence of images of a task performed by the worker.

DETAILED DESCRIPTION OF EMBODIMENTS OF THE INVENTION

Figure 1:
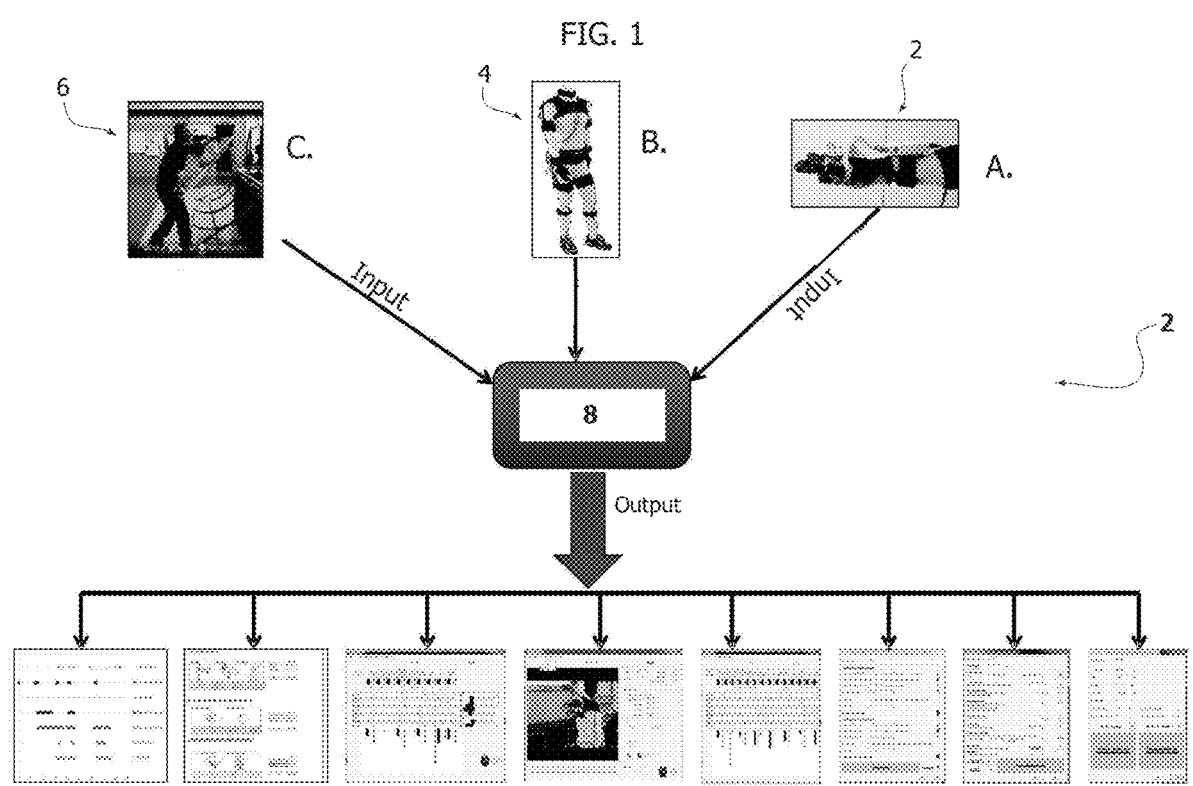
FIG. 1 is a block diagram provided by way of example of a system according to an embodiment of the invention.

With reference to FIG. 1, number 1 designates as a whole a system according to the invention for analysis of the movements of the human body or parts thereof, in particular for analysis of the movements of a worker during execution of the tasks entrusted to him, and more in particular for analysis of the movements of an assembly-line worker in the automotive sector.

The system 1 comprises:
- at least one device 2 (FIG. 1A), preferably provided as a wearable sensorized glove, for detecting movements made by a worker's hand and forces applied thereby;
- a wearable network 4 of sensors (FIG. 1B), preferably inertial sensors, where the sensors are located in the network so as to be associated to corresponding joints of the human body; preferably, the wearable network is incorporated in a garment or kit of garments such, such as a pair of overalls;
- an image-acquisition system 6 (FIG. 1C) including one or more cameras configured for acquisition of images of the worker within the working area for the purposes of subsequent ergonomic assessment; in the case of provision of a number of cameras, different cameras may be associated to different shooting angles; and
- a processing unit 8 configured for receiving data and/or signals from the sensorized glove 2, and/or from the wearable sensor network 4, and/or from the image-acquisition system 6, and configured for processing said data and/or signals to estimate ergonomic indicators, and/or to obtain local information on efforts made and/or posture.

Figure 2:
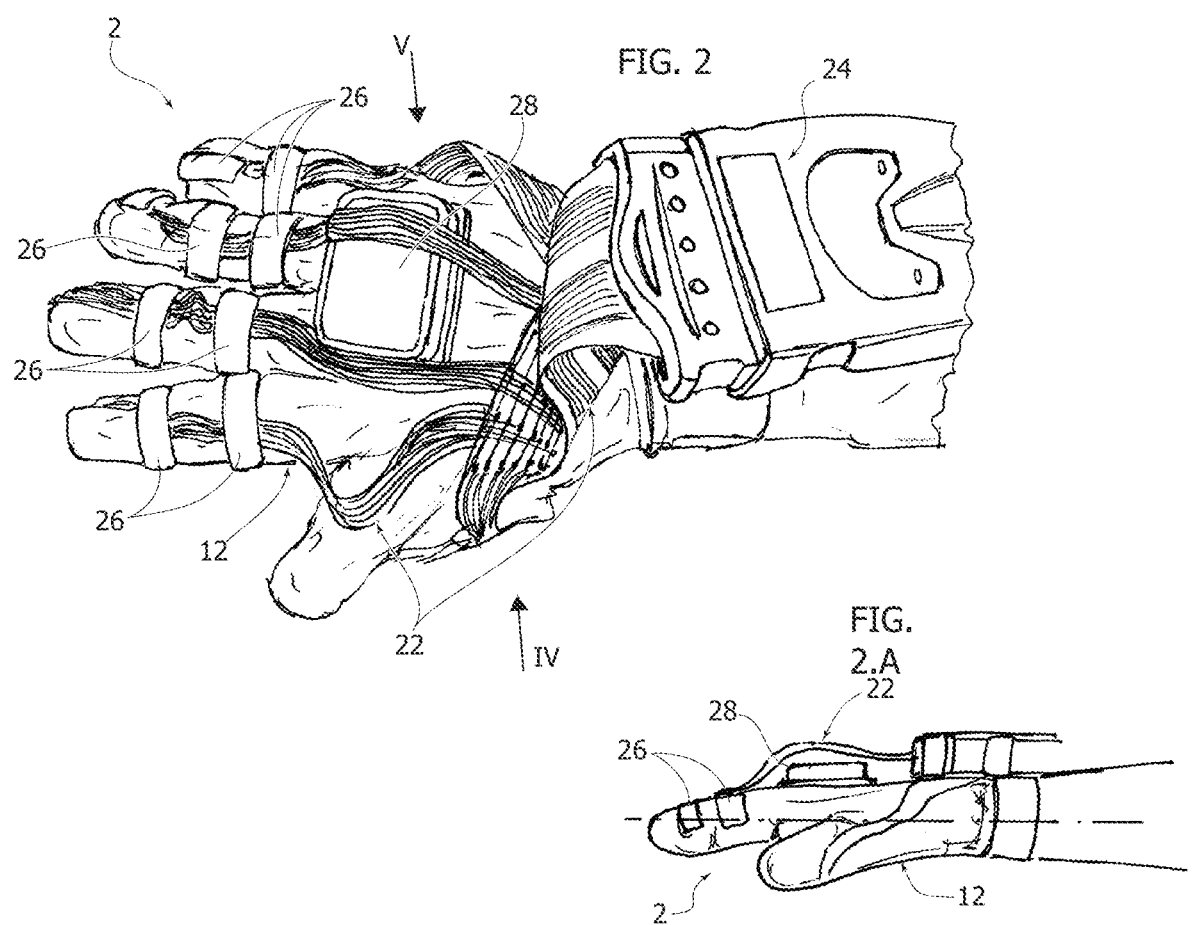
FIG. 2 is an overall view of a device for collecting force and position data that can be applied to the hand of a worker, in particular a line operator.

With reference to FIG. 2, an embodiment of the device 2 according to the invention is illustrated therein. The device is provided as a double-walled sensorized glove. In particular, the glove 2 includes an inner glove 10 (FIG. 3), and an outer glove 12 (FIGS. 2, 2A, 4, 5—in all cases the presence of the glove 10 is implicit).

Figure 3:
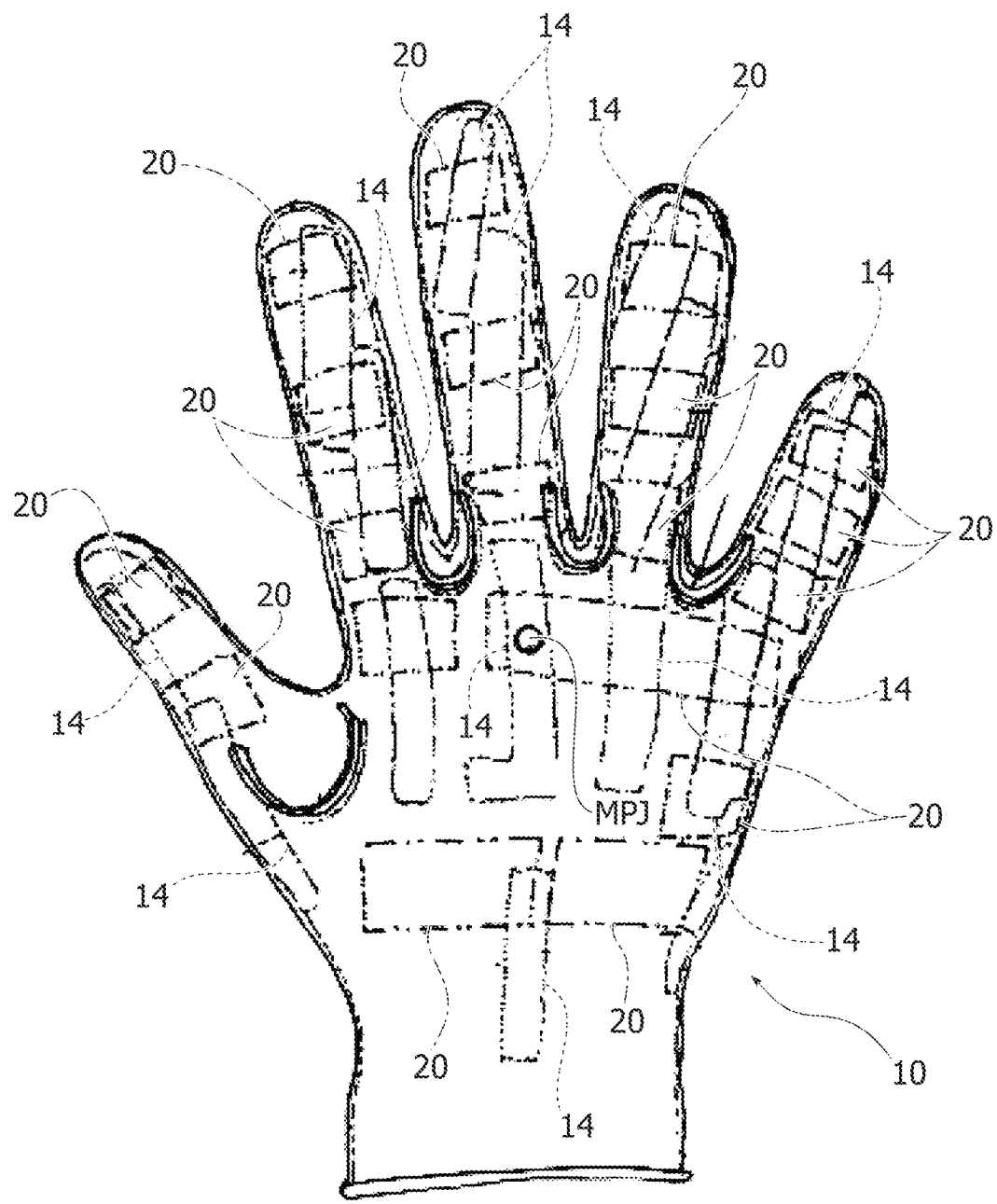
FIG. 3 is a top plan view of a component of the device of FIG. 2.
Figure 6:
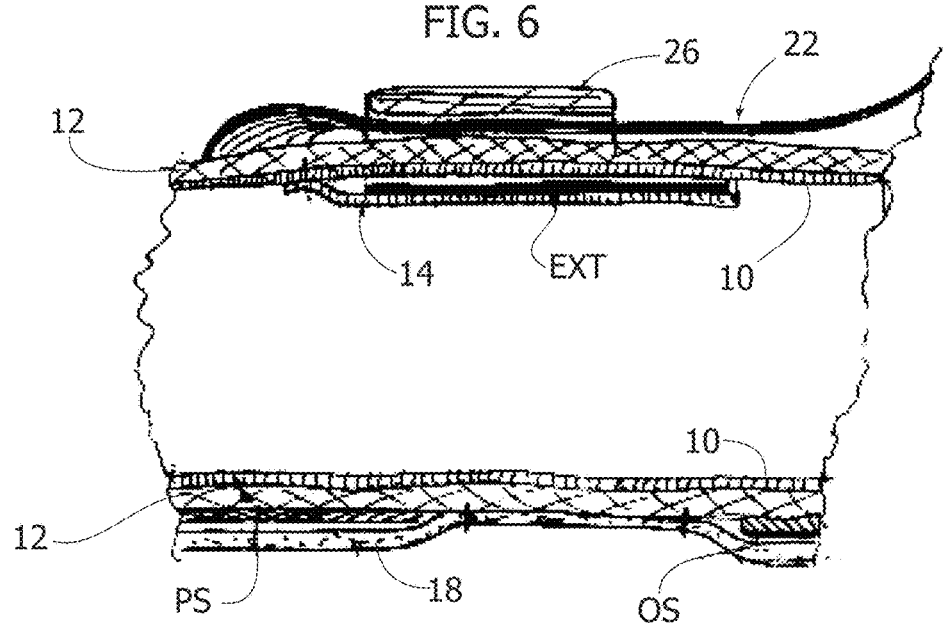
FIG. 6 is a cross-sectional view provided by way of example of the device of FIG. 2, in particular taken along an axis of a finger.

With reference to FIG. 3, the inner glove 10 (which may for example be a sensorized glove commercially available under the brand name Cyberglove®) is configured for detecting and transmitting to the processing unit 6 data on the position and relative movements of the various parts of the human hand: carpus, metacarpus, and phalanges. For this purpose, the glove 10 includes a first plurality of pockets 14, which are sewn inside the glove 10 so as to follow more faithfully the movements of the hand without running the risk of following the deformations of the glove, preferably have a rectangular shape, and house inside them corresponding linear extensometers EXT (FIG. 6).

A second plurality of pockets 16, which are substantially U-shaped, are, instead, sewn on the outer surface of the glove 10 and house corresponding linear extensometers, which, on account of the U shape of the pockets, are able to detect the relative movements of the various parts of the hand, for example in the palmar plane (for example, movements of divarication of the fingers).

Figure 3A:
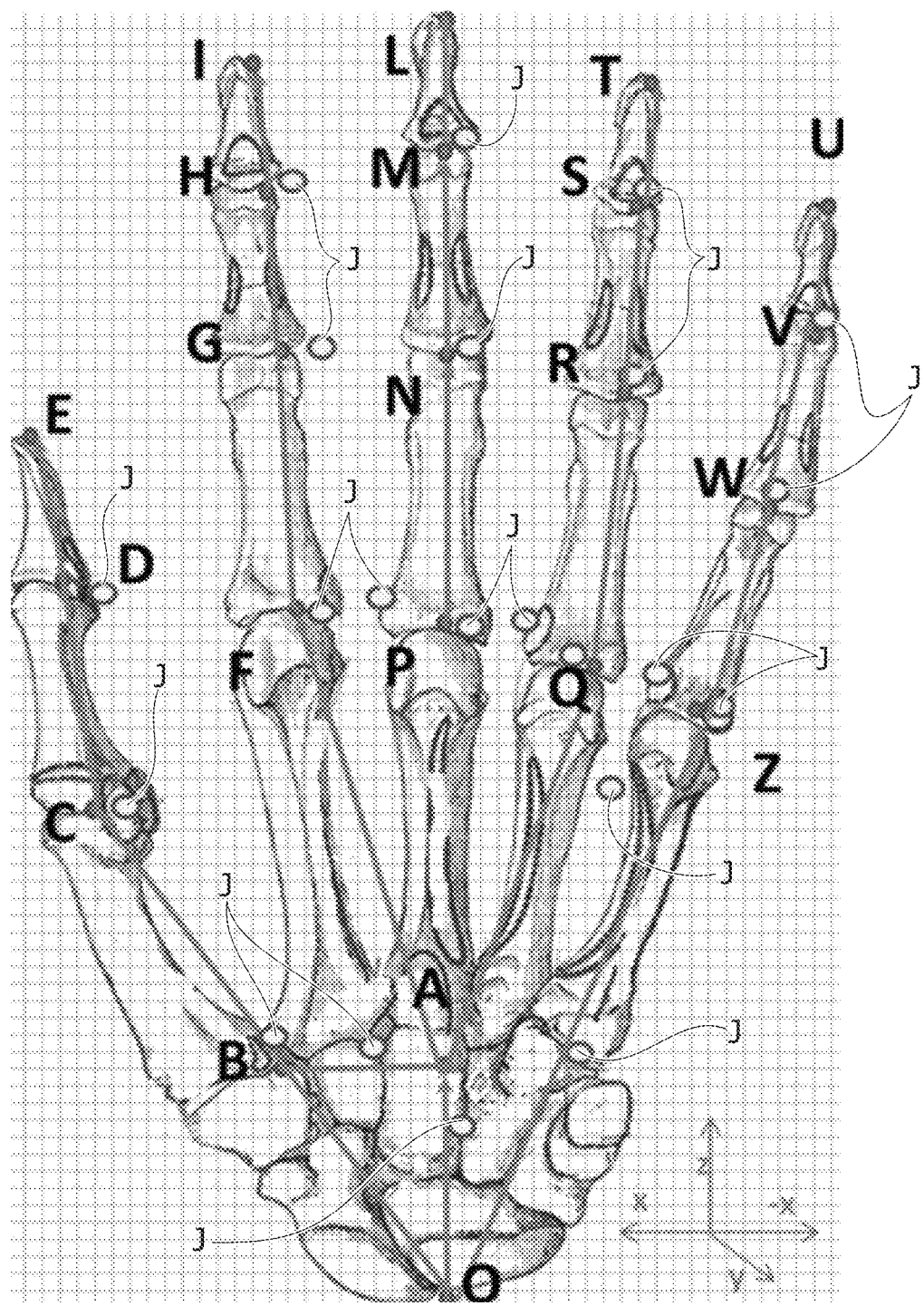
FIG. 3A illustrates a correlation between an arrangement of sensor elements on the device of FIG. 3A and a reference human anatomy.
Figure 8:
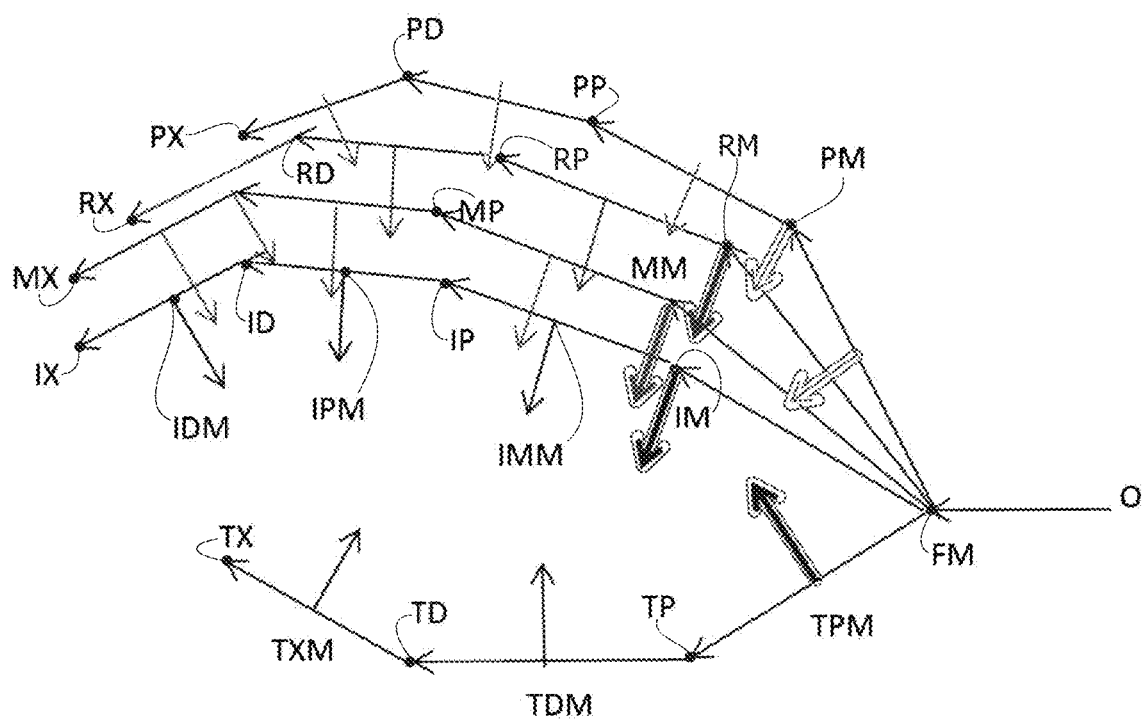

FIG. 3A illustrates an example of vector mapping that can be used for the interface with the data supplied by the extensometers installed on the glove 10. This vector map, as will be seen hereinafter with reference to FIG. 8, is at the basis of a method for detecting the movements of the worker's hand according to the invention.

The vector map of FIG. 3A moreover presents a local system of axes that can preferably be adopted for referencing the co-ordinates of movement detected by the extensometers of the glove 10. In particular, the plane XZ is a palmar plane, the plane XY is a transverse plane, whereas the plane YZ is a sagittal plane.

Figure 5:
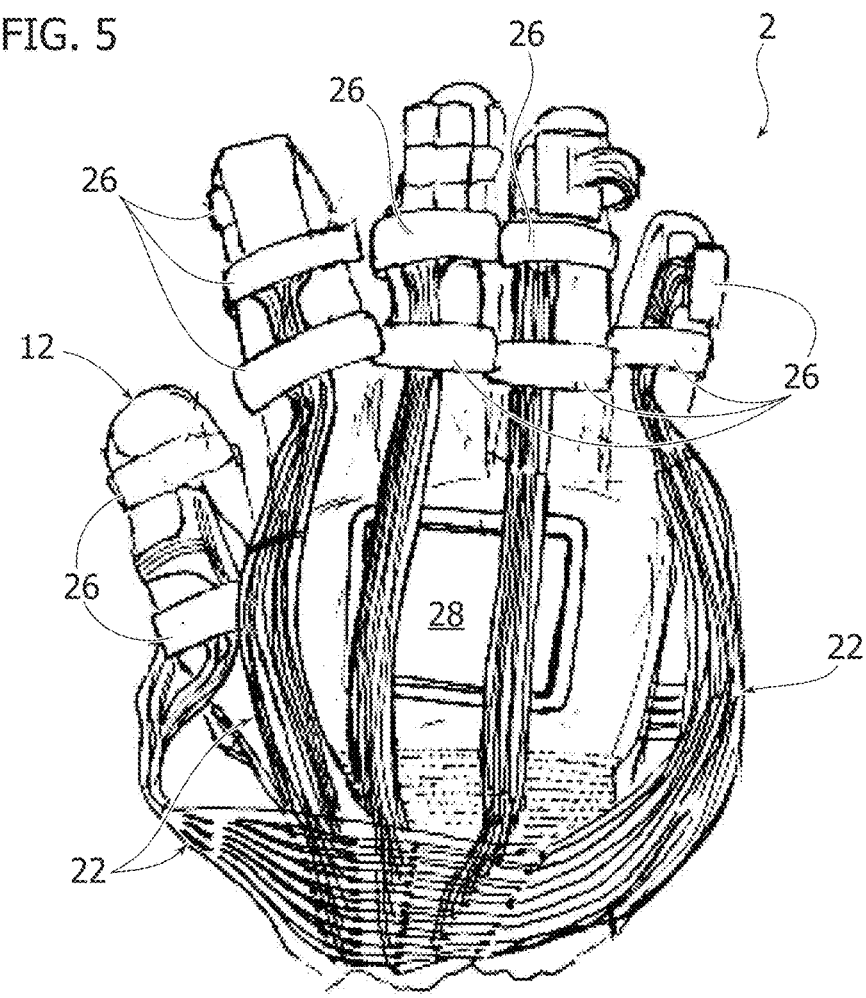
FIG. 5 is a view according to the arrow V of FIG. 2.

With reference to FIGS. 2, 4, and 5, the outer glove 12 is made of textile material, for example elasticated cotton (preferably, like the glove 10) both on the palm—FIG. 4—and on the back—FIG. 5. This renders coupling of the outer glove 12 with the inner glove 10 more stable and precise. Applied on the palm 4 is a second layer 18 made of anti-slip material designed to improve the grip, for example Alcantara®.

Sewn (or otherwise applied) in the (outer) layer 18 are a plurality of pockets 20 of a preferably quadrangular shape configured for housing a corresponding pressure sensor PS (see FIG. 4A). In order to facilitate insertion of the sensor—which is substantially provided on a film support—each pocket 20 is not sewn on at least one of the sides (preferably it is sewn only on three sides when the pocket is quadrangular). Moreover, a polyamide layer is preferably provided on the portion of outer glove 12 corresponding to the palm, underneath the layer 18. The polyamide layer facilitates insertion of the sensors in the pockets 20.

Each pressure sensor forms part of a sensor network 22 having a layout such as to enable application of the individual sensors PS in predetermined areas of the hand. An example of such a sensor network is illustrated in FIG. 4A (in a splayed-out, substantially tree-shaped, configuration), and may preferably correspond to a product commercially available under the brand name Tekscan®; it is moreover partially visible in FIG. 2. The sensor network 22 includes a plurality of electrical connections, connected to which are the pressure sensors PS and where the electrical connections all lead to an interface unit 24, which enables exchange of data with the processing unit 8 or in any case with any purposely configured processing unit.

To ensure a more orderly and rational routing of the electrical connections that form part of the sensor network 22, applied on the outer glove 12, in particular on the back, in the area of the fingers, are one or more bands 26. The bands 26 are preferably made of self-adhesive material, such as Velcro® and withhold the electrical connections of the network 22, preferentially routing them along the fingers of the outer glove 12. According to an advantageous aspect of the present invention, the bands 26 may extend circumferentially as far as an opening of one of the pockets 20 in such a way as to obstruct it at the moment when they are positioned on the outer glove 12. This reduces or eliminates the possibility of accidental exit of the pressure sensors of the network 22.

Once again preferably, the outer glove 12 may be provided with inserts obtained with an elastic ribbon in positions corresponding to the fingers, oriented in a longitudinal direction of the fingers themselves. This enables a better adaptation to a range of different finger thicknesses.

The back (dorsal surface) of the outer glove 12 is moreover provided with a fixing portion made of self-adhesive material—for example Velcro—whereby it is possible to fix in a rapid way an inertial sensor 28, which makes it possible to provide the glove 2 with an absolute position reference in the case where the glove is used in the framework of a more complex system, such as the one that will be described with reference to the subsequent FIGS. 14 and 15.

The interface 24 is fixed with a band on the wrist of the worker, as illustrated in FIG. 2.

With reference once again to FIG. 3, superimposed on the representation of the inner glove 10 is the map of the pockets 20 (illustrated with a dashed and double-dotted line) so as to highlight the relative position between the linear extensometers EXT in the pockets 14, 16 and the pressure sensors PS in the pockets 20.

There now follows a description of a preferred mode of integration between the data of position/movement supplied by the sensors (extensometers EXT) on the inner glove 10 and the pressure data supplied by the sensors PS on the glove 12. It is possible to set in communication the sensors of the glove 10 and of the glove 12 using a data-transmission protocol, for example a data-transmission protocol of the UDP type.

The sensors on the glove 10 supply as output data the angles and co-ordinates for twenty-two (22) joints of the hand identified by the reference J in FIG. 3A. However, they are not configured in such a way as to supply information on the co-ordinates of the tips of the fingers. The latter is a datum that needs to be calculated.

Calculation of the Co-Ordinates of the Tips of the Fingers

Figure 7:
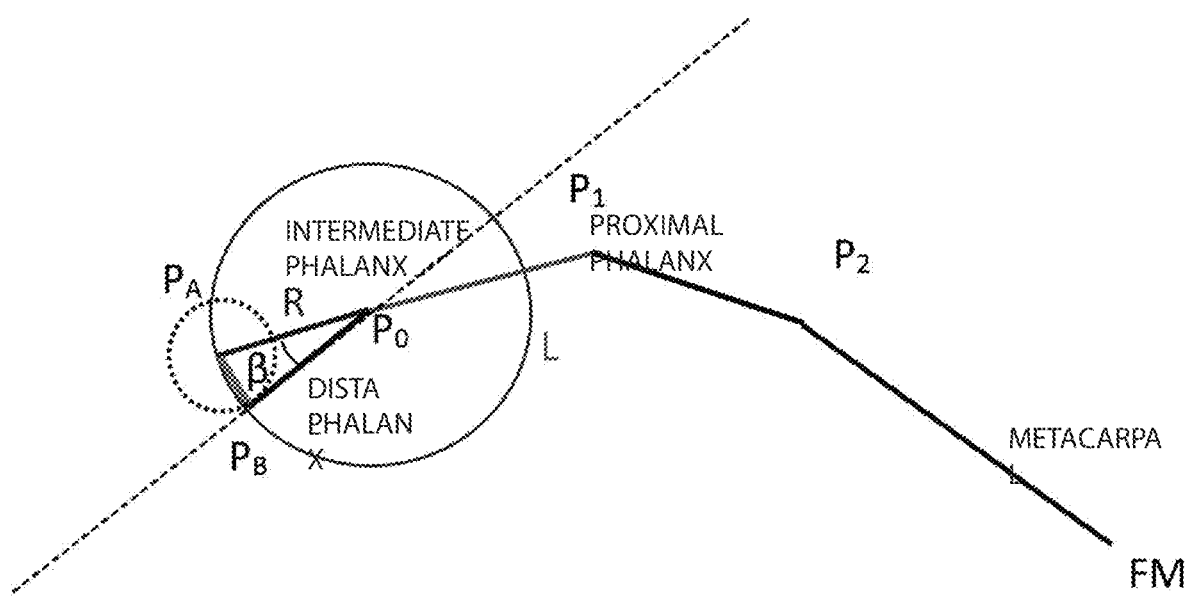
FIGS. 7 and 8 are functional schemes that illustrate the premises of a method according to the invention.

For the purposes of this calculation the hypotheses listed below are adopted (see FIG. 7).

i) Reference nomenclature for the segments of the fingers, starting from the metacarpals: proximal phalanx (segment at the root), intermediate phalanx (intermediate segment), and distal phalanx (top segment).

ii) It is assumed that there are five (5) distinct balls of known radius $R_n$. The value of the radius $R_n$ is equal to a pre-set length for each distal phalanx (the lengths are estimated on the statistically most representative dimensions of distal phalanges), n being an index that ranges from 1 to 5. Each of the five balls is centred on the end of a corresponding intermediate phalanx, hence in the points TD, ID, MD, RD, and PD (the first letters standing for "Thumb", "Index finger", "Middle finger", "Ring finger", and "Pinky", respectively), see FIG. 8.

iii) The abduction of the distal phalanx with respect to the intermediate phalanx and the abduction of the intermediate phalanx with respect to the proximal phalanx are assumed as being zero.

With reference once again to FIG. 7, assuming that each finger is perfectly straight, the tip of each finger ($P_A$) is a point that belongs to the straight line passing through the two ends of the intermediate phalanx ($P_1$ and $P_0$), where $P_0$ is the end point where the intermediate and distal phalanges meet. This condition may be written in the form of a system of equations (satisfied also by $P_A$) and makes it possible to express the co-ordinates y and z as a function of x (the reference system is the same as the one used for the inner glove 10).

$$(x-x_0)/(x_1-x_0)=(z-z_0)/(z_1-z_0)$$

$$(x-x_0)/(x_1-x_0)=(y-y_0)/(y_1-y_0)$$

$P_A$ also belongs to the ball centred in $P_0$ and having radius R, which is a known (imposed) quantity and corresponds to the length of the distal phalanx.

Physiologically the distal phalanx $P_A$-$P_0$ is shorter than the intermediate phalanx $P_1$-$P_0$; hence, we may assume R<L $$R=\text{dist}(P_A,P_0)=[(x_A-x_0)^2+(y_A-y_0)^2+(z_A-z_0)^2]^{1/2}$$

$$L=\text{dist}(P_1,P_0)=[(x_1-x_0)^2+(y_1-y_0)^2+(z_1-z_0)^2]^{1/2}$$

Note: of the two solutions, the one with positive sign is to be chosen, given that we are dealing with lengths.

By intersecting the aforesaid straight line (passing through the two ends of the intermediate phalanx) with the ball of radius R centred in $P_0$, two points are found, one of which is the point $P_A$.

Expressing, using the straight-line equations provided above, y and z as a function of x $$(x-x_0)^2[1+(y_1-y_0)^2/(x_1-x_0)^2+(z_1-z_0)^2/(x_1-x_0)^2]=R^2$$

we obtain the solutions $x_{A1}$ and $x_{A2}$:

$$x_{A1}=x_0+R/L, \text{ and } x_{A2}=x_0-R/L$$

The correct solution will be the one whereby the following condition is satisfied:

$$\text{dist}(P_A,P_1)>L$$

where $$P_{A1}=P(x_{A1},y_{A1},z_{A1})=(x_0+R/L,y_0+(y_1-y_0)(x_{A1}-x_0)/(x_1-x_0),z_0+(z_1-z_0)(x_{A1}-x_0)/(x_1-x_0))$$

$$P_{A2}=P(x_{A2},y_{A2},z_{A2})=(x_0-R/L,y_0(y_1-y_0)(x_{A2}-x_0)/(x_1-x_0),z_0+(z_1-z_0)(x_{A2}-x_0)/(x_1-x_0))$$

Since $P_A$ is known, from trigonometry we obtain $$\text{dist}(P_A,P_B)=2R\sin(\beta/2)=R_1$$

where $\beta$ is the angle of flexion supplied by the corresponding extensometer EXT.

To find the co-ordinates of $P_B$, the ball centred in $P_A$ with radius equal to the distance between $P_A$ and $P_B$, dist($P_A$,$P_B$), is considered:

$$[(x_B-x_A)^2+(y_B-y_A)^2(z_B-z_A)^2]=\text{dist}^2(P_A,P_B)=R_1^2$$

The above formula may also be re-written so as to obtain the co-ordinates of $P_B$ ($x_B$, $y_B$, $z_B$) as follows:

$$[(x_B-x_0)-(x_A-x_0)]^2+[(y_B-y_0)-(y_A-y_0)]^2+[(z_B-z_0)-(z_A-z_0)]^2=R_1^2$$

$$[(x_B-x_0)-(x_A-x_0)]^2+[(y_B-y_0)-(y_A-y_0)]^2+[(z_B-z_0)-(z_A-z_0)]^2=R_1^2$$

$$(x_B-x_0)^2-2(x_B-x_0)(x_A-x_0)+(x_A-x_0)^2+(y_B-y_0)^2-2(y_B-y_0)(y_A-y_0)+(y_A-y_0)^2+(z_B-z_0)^2-2(z_B-z_0)(z_A-z_0)+(z_A-z_0)^2=R_1^2$$

$$\text{dist}^2(P_B,P_0)+\text{dist}^2(P_A,P_0)-2[(x_B-x_0)(x_A-x_0)+(y_B-y_0)(y_A-y_0)+(z_B-z_0)(z_A-z_0)]=R_1^2$$

$$R^2+R^2-2x_B(x_A-x_0)+2x_0(x_A-x_0)-2y_B(y_A-y_0)+2y_0(y_A-y_0)-2z_B(z_A-z_0)+2z_0(z_A-z_0)=R_1^2=4R^2\sin^2(\beta/2)$$

Imposing that $P_B$ lies in the plane $\pi$(ax+by +cz+d=0) passing through the points $P_0$, $P_1$, $P_2$, we have $$a=-2x_B(x_A-x_0) => x_B=\text{to}/2(x_0-x_A)$$

$$b=-2y_B(y_A-y_0) => y_B=b/2(y_0-y_A)$$

$$c=-2z_B(z_A-z_0) => z_B=c/2(z_0-z_A)$$

whence $$P_B=(x_B,y_B,z_B)=(a/2(x_0-x_A),b/2(y_0-y_A),c/2(z_0-z_A))$$

This is an approximate solution, above all as regards definition of $P_A$ and $P_B$ for the thumb, but for the purposes of the calculation in question it is deemed acceptable.

Calculation of the Force Vectors on the Hand

It is necessary in the first place to define the reference direction and sense for the force vectors, which are each assumed as being applied in the middle point of each phalanx, or else—in the case of the palm—in the points associated to vectors represented by bordered arrows in FIG. 8.

To define the direction, the intersection between the plane $\pi$ passing through the three points of the three phalanges (e.g., the point IM between the metacarpal and the proximal phalanx, the point IP between the proximal phalanx and the intermediate phalanx, and the point ID between the intermediate phalanx and the distal phalanx) and the plane $\pi'$ passing through each phalanx in the middle point and orthogonal to $\pi$ is sought (this implies the condition of orthogonality to the phalanx: given that the phalanx is not flexible and is contiguous to the other phalanges, the plane orthogonal to the plane containing the phalanx is orthogonal to the phalanx).

Imposing that $\pi$ passes through the points IM, IP, and ID, the equation of the plane (ax+by+cz+d=0) becomes $$(x-x_{IM})\cdot[(y_{IP}-y_{IM})\cdot(z_{IP}-z_{IM})-(y_{IP}-y_{IM})\cdot(z_{IP}-z_{IM})]+(y-y_{IM})\cdot[(x_{IP}-x_{IM})\cdot(z_{ID}-z_{IM})-(x_{ID}-x_{IM})\cdot(z_{IP}-z_{IM})]+(z-z_{IM})\cdot[(x_{IP}-x_{IM})\cdot(y_{IP}-y_{IM})-(x_{ID}-x_{IM})\cdot(y_{IP}-y_{IM})]=0$$

whence $$a=(y_{IP}-y_{IM})\cdot(z_{IP}-z_{IM})-(y_{ID}-y_{IM})\cdot(z_{IP}-z_{IM})$$

$$b=(x_{IP}-x_{IM})\cdot(z_{IP}-z_{IM})-(x_{ID}-x_{IM})\cdot(z_{IP}-z_{IM})$$

$$c=(x_{IP}-x_{IM})\cdot(y_{ID}-y_{IM})-(x_{ID}-x_{IM})\cdot(y_{IP}-y_{IM})$$

$$d=-x_{IM}\cdot[(y_{IP}-y_{IM})\cdot(z_{IP}-z_{IM})-(y_{ID}-y_{IM})\cdot(z_{IP}-z_{IM})]-y_{IM}\cdot[(x_{IP}-x_{IM})\cdot(z_{ID}-z_{IM})-(x_{ID}-x_{IM})\cdot(z_{IP}-z_{IM})]+-z_{IM}\cdot[(x_{IP}-x_{IM})\cdot(y_{ID}-y_{IM})-(x_{ID}-x_{IM})\cdot(y_{IP}-y_{IM})]$$

To determine the second plane $\pi'$ orthogonal to the plane $\pi$, it is sufficient to impose the condition of orthogonality for the two vectors that identify each plane (normal vectors, i.e., their scalar product must be zero) and passage of the second plane $\pi'$ a'x+b'y+c'z+d'=0 through the middle point of the phalanx in question (for example, the point IMM).

A vector that satisfies the condition of orthogonality to the vector (a, b, c) may also belong to the plane defined previously, and hence also the phalanx segment (for example, IP-IM) may constitute such a vector:

$$\text{IP-IM}=[(x_{IP}-x_{IM}),(y_{IP}-y_{IM}),(z_{IP}-z_{IM})]$$

Imposing passage through the middle point of the phalanx (IMM=$[(x_{IP}+x_{IM})/2, (y_{IP}+y_{IM})/2, (z_{IP}+z_{IM})/2]$) it is possible to write the equation of the second plane as $$a'(x_{IMM})+b'(y_{IMM})+c'(z_{IMM})+d'=0$$

$$(x_{IP}-x_{IM})\cdot(x_{IP}+x_{IM})/2+(y_{IP}-y_{IM})\cdot(y_{IP}+y_{IM})/2++(z_{IP}-z_{IM})\cdot(z_{IP}+z_{IM})/2+d'=0=>$$

$$a'=(x_{IP}-x_{IM})$$

$$b'=(y_{IP}-y_{IM})$$

$$c'=(z_{IP}-z_{IM})$$

$$d'=(x_{IM}^2-x_{IP}^2)/2+(y_{IM}^2-y_{IP}^2)/2+(z_{IM}^2-z_{IP}^2)/2$$

Gathering the equations of the two planes into a system, we obtain as solution the intersection straight line that identifies the direction of the vector and that passes through the middle point of the phalanx (IMM in the example).

Since it is necessary to identify also a sense to define the force vector, it is possible to consider the point of intersection between the straight line and the ball having a radius equal to the modulus of the force exerted in the point (there are two such points of intersection).

This point can be defined as the South pole of the ball centred in the middle point $P_{IMM}$ [IMM] and having a radius R equal to the summation of the pressures detected by the sensors PS in points corresponding to the pockets 20, i.e., in the points associated to the finger-tips.

In cartesian co-ordinates, the ball of radius R centred in $P_{IMM}$ [IMM] will have the following equation:

$$(x-x_{IMM})^2+(y-y_{IMM})^2+(z-z_{IMM})^2=R^2$$

The points of intersection with the intersection straight line of the two previous planes define the ends of the two vectors comprised between which is the vector sought (definition of sense of the force).

Gathering the equations of the two planes into a system, from the first equation we obtain x=(−by−cz−d)/a, and substituting in the equation of the second plane y=(−a'x−c'z−d')/b', it is possible to express both y and x as a function of z to obtain $$y=z(a'c-c'a)/(b'a-ab)+(a'd-d'a)/(a'c-c'a)=Az+B$$

$$x=z[(b(a'c-c'a)+c(b'a-a'b))/a(a'b-b'a)]+[(b(d'a-a'd)+d(c'a-a'c))/a(a'c-c'a)]=Cz+D$$

where $$A=(a'c-c'a)/(b'a-ab')$$

$$B=(a'd-d'a)/(a'c-c'a)$$

$$C=[(b(a'c-c'a)+c(b'a-a'b))/a(a'b-b'a)]$$

$$D=[(b(d'a-a'd)+d(c'a-a'c))/a(a'c-c'a)]$$

The above formulation is to be used only in the case where a≠0 and a'c≠c'a and a'b≠b'a.

Substituting x and y in the equation of the ball, we obtain the two co-ordinates $z_1$ and $z_2$ (belonging to the set of the real numbers; in any case, it is advisable to check that the discriminant of the equation is positive, i.e., $(\beta^2-4\alpha\gamma)>0$).

Assuming $$\alpha=(C^2+A^2+1)$$

$$\beta=2[C(D-x_{IMM})+A(B-y_{IMM})-z_{IMM}]$$

$$\gamma=-R^2+(D-x_{IMM})^2+(B-y_{IMM})^2+z_{IMM}^2$$

we obtain $$z_1=[-\beta-(\beta^2-4\alpha\gamma)^{1/2}]/2\alpha$$

$$z_2=[\beta-(\beta^2-4\alpha\gamma)^{1/2}]/2\alpha$$

whence $$P_1=P(x_1,y_1,z_1)=(C[-\beta-(\beta^2-4\alpha\gamma)^{1/2}]/2\alpha+D,A[-\beta-(\beta^2-\to\alpha\gamma)^{1/2}]/2\alpha+B,[-\beta-(\beta^2-4\alpha\gamma)^{1/2}]/2\alpha)$$

$$P_2=P(x_2,y_2,z_2)=(C[+\beta(\beta^2-4\alpha\gamma)^{1/2}]/2\alpha+D,A[+\beta--(\beta^2-4\alpha\gamma)^{1/2}]/2\alpha+B,[\beta-(\beta^2-4\alpha\gamma)^{1/2}]/2\alpha)$$

The correct triad will be the one that has the shorter distance from the co-ordinate corresponding to the tip of the thumb $P_{TX}$, namely $$P_{IMMF}(x,y,z)=\min(\text{dist}(P_1,P_{TX}),\text{dist}(P_2,P_{TX}))$$

where:

$$dist(P_1, P_{TX}) = [(x_1 - x_{IMMF})^2 + (y_1 - y_{IMMF})^2 + (z_1 - z_{IMMF})^2]^{1/2}$$

and $$dist(P_2, P_{TX}) = [(x_2 - x_{IMMF})^2 + (y_2 - y_{IMMF})^2 + (z_2 - z_{IMMF})^2]^{1/2}$$

For it to be a plane in cartesian form, all the coefficients that identify it (vector orthogonal to the plane) can never simultaneously be zero, and hence we can never simultaneously have a=b=c=0.

If a=0, only the following interesting and non-degenerate cases may be found:
a=b=0 and c≠0
a=0 and b≠0 and c of any value With a=b=0 and c≠0, we have z=−d/c, and the two sub-cases with b'≠0 and b'=0 will be possible.

If a=b=0 and c≠0, substituting z in π' makes it possible to obtain y as a function of x (or x as a function of y) according to whether either a' or b' are possibly zero.

If a'=0 and b'≠0 we obtain y=(c'd−d'c)/cb' and z=−d/c, which, once substituted in the equation of the ball, will yield the solutions $x_1$ and $x_2$ $$x_1 = x_{IMM_{1/2}} - [(R^2 - (-d/c - z_{IMM})^2 - ((c'd - cd')/cb' - y_{IMM})^2]$$

$$x_2 = x_{IMM_{1/2}} + [(R^2 - (-d/c - z_{IMM})^2 - ((c'd - cd')/cb' - y_{IMM})^2]$$

whence $$P_1 = P(x_1, y_1, z_1) = (x_{IMM} - [(R^2 - (-d/c - z_{IMM})^2 - ((c'd - cd')/cb' - y_{IMM})^2]^{1/2}, (c'd - cd')/cb', -d/c)$$

$$P_2 = P(x_2, y_2, z_2) = (x_{IMM} + [(R^2 - (-d/c - z_{IMM})^2 - ((c'd - cd')/cb' - y_{IMM})^2]^{1/2}, (c'd - cd')/cb', -d/c)$$

The correct triad will be the one with the shorter distance from the co-ordinate corresponding to the tip of the thumb $P_{TX}$, namely $$P_{IMMF}(x, y, z) = \min(dist(P_1, P_{TX}), dist(P_2, P_{TX}))$$

where:

$$dist(P_1, P_{TX}) = [(x_1 - x_{IMMF})^2 + (y_1 - y_{IMMF})^2 + (z_1 - z_{IMMF})^2]^{1/2}$$

and $$dist(P_2, P_{TX}) = [(x_2 - x_{IMMF})^2 (y_2 - y_{IMMF})^2 (z_2 - z_{IMMF})^2]^{1/2}$$

If a'≠0 and b'=0, we obtain $$x = (c'd - d'c)/a'c \text{ and } z = -d/c$$

which, substituted in the equation of the ball, yields the solutions $y_1$ and $y_2$ $$y_1 = y_{IMM} - [(R^2 - (-d/c - z_{IMM})^2 - ((d'c - cd')/ca' - x_{IMM})^2]^{1/2}$$

$$y_2 = y_{IMM} + [(R^2 - (-d/c - z_{IMM})^2 - ((d'c - cd')/ca' - x_{IMM})^2]^{1/2}$$

and hence $$P_1 = P(x_1, y_1, z_1) = (y_{IMM} - [(R^2 - (-d/c - z_{IMM})^2 - ((d'c - cd')/ca' - x_{IMM})^2]^{1/2}, (c'd - d'c)/a'c, -d/c)$$

$$P_2 = P(x_2, y_2, z_2) = (y_{IMM} - [(R^2 - (-d/c - z_{IMM})^2 - ((d'c - cd')/ca' - x_{IMM})^2]^{1/2}, (c'd - d'c)/a'c, -d/c)$$

The correct triad will be the one that has the shorter distance from the co-ordinate corresponding to the tip of the thumb $P_{TX}$, namely $$P_{IMMF}(x, y, z) = \min(dist(P_1, P_{TX}), dist(P_2, P_{TX}))$$

where:

$$dist(P_1, P_{TX}) = [(x_1 - x_{IMMF})^2 + (y_1 - y_{IMMF})^2 + (z_1 - z_{IMMF})^2]^{1/2}$$

and $$dist(P_2, P_{TX}) = [(x_2 - x_{IMMF})^2 + (y_2 - y_{IMMF})^2 (z_2 - z_{IMMF})^2]^{1/2}$$

Following upon this calculation, there are hence known the middle points of application of the forces on the various areas of the hand that derive from the readings made by the sensors PS, with respect to the positions of the joints J, the postural data of which are collected by the extensometers EXT.

This enables definition of the direction of the force itself.

Operation of the glove 2 is described in what follows.

The glove 2 can be used for obtaining postural information on the hand (when the inertial sensor 28 is present on the glove), for obtaining the direction of the resultant of force when associated thereto is the reading of the pressure intensities with corresponding orientation of the surface on which pressure acts (direction of the force on the various sensors), and chiefly for recognising the type of grasp exerted by the worker when the postures of the fingers are associated to the pressure exerted by the fingers most involved in the posture being detected.

Figure 10C:
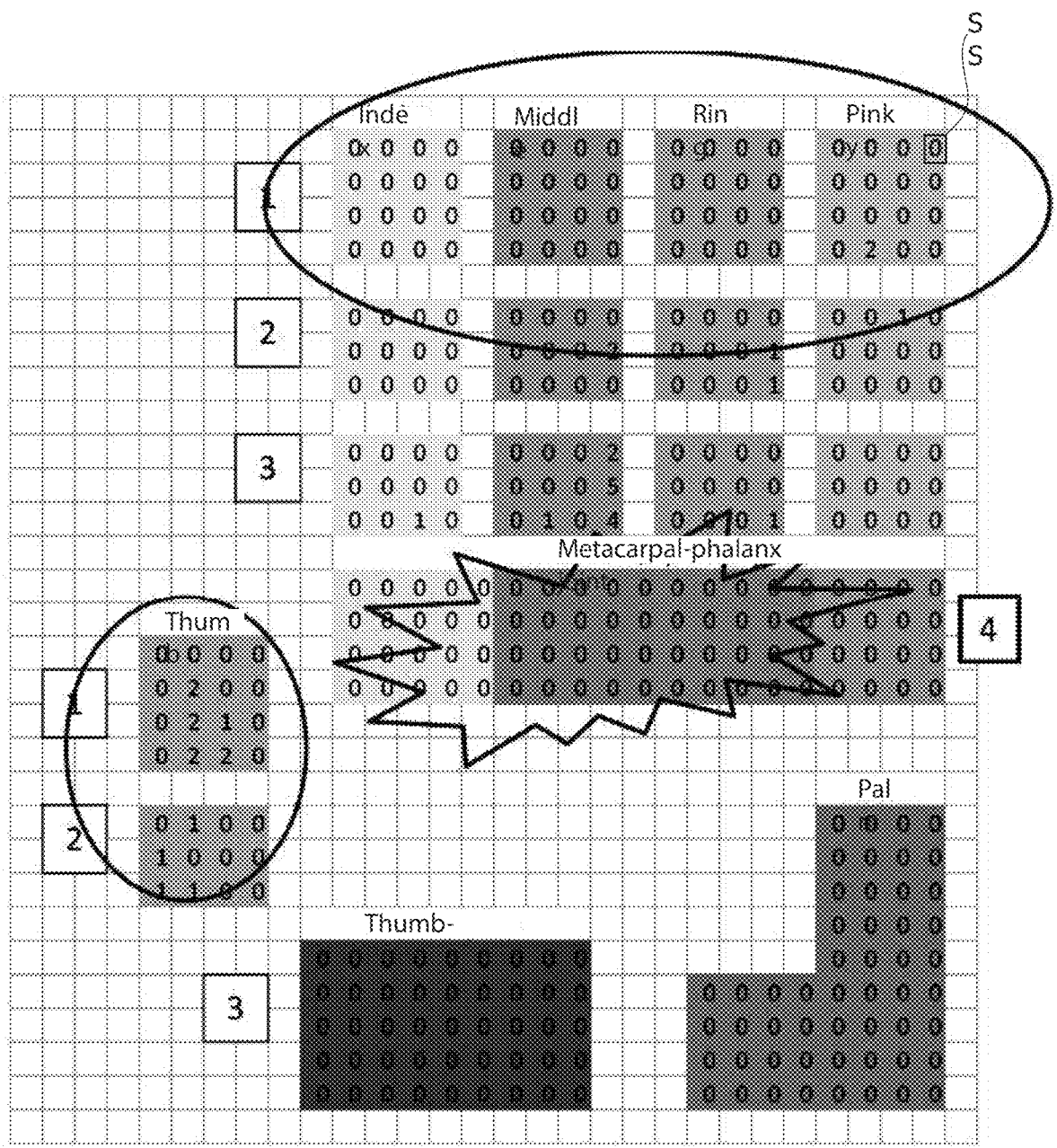
Figure 11C:
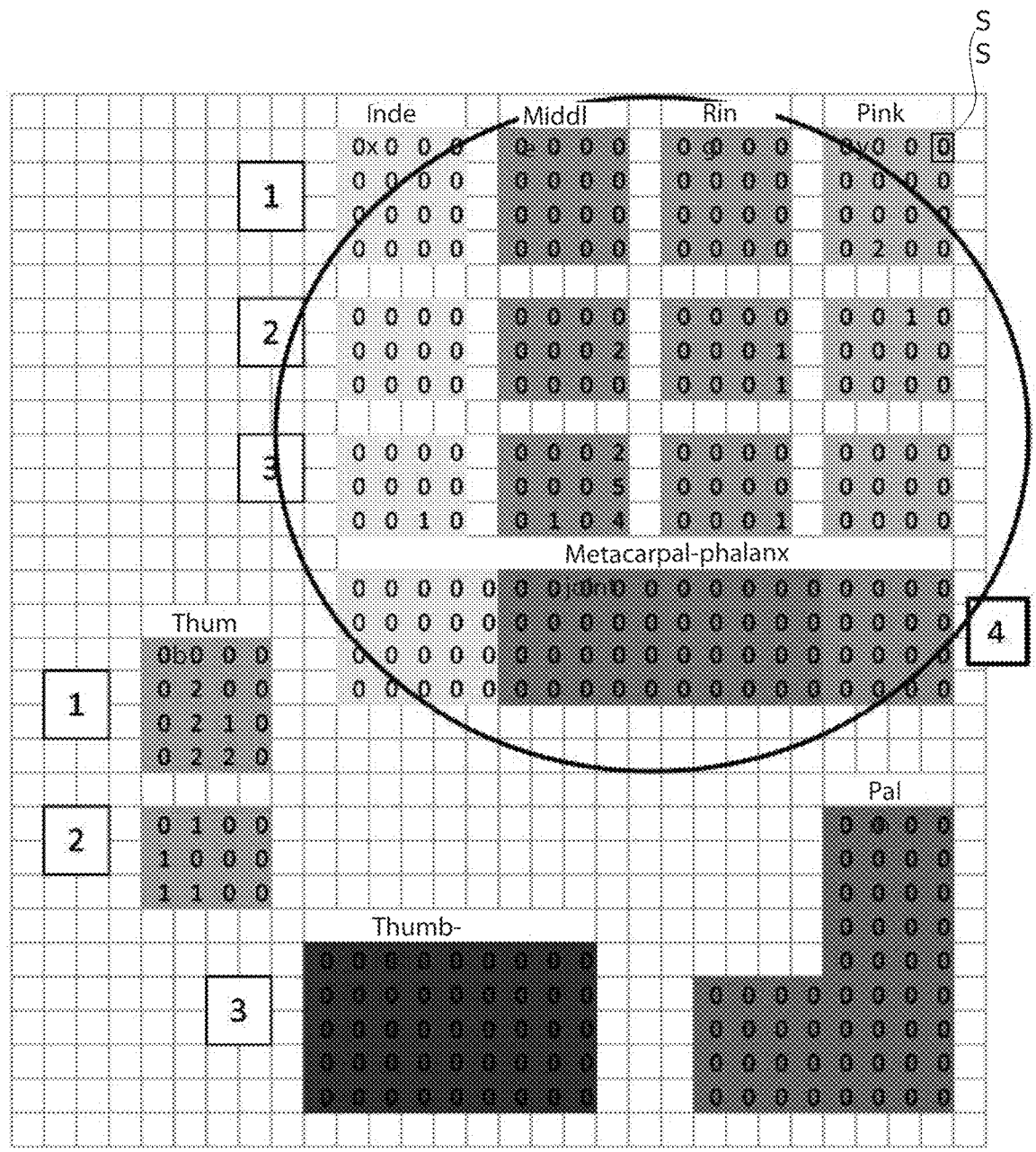
Figure 12C:
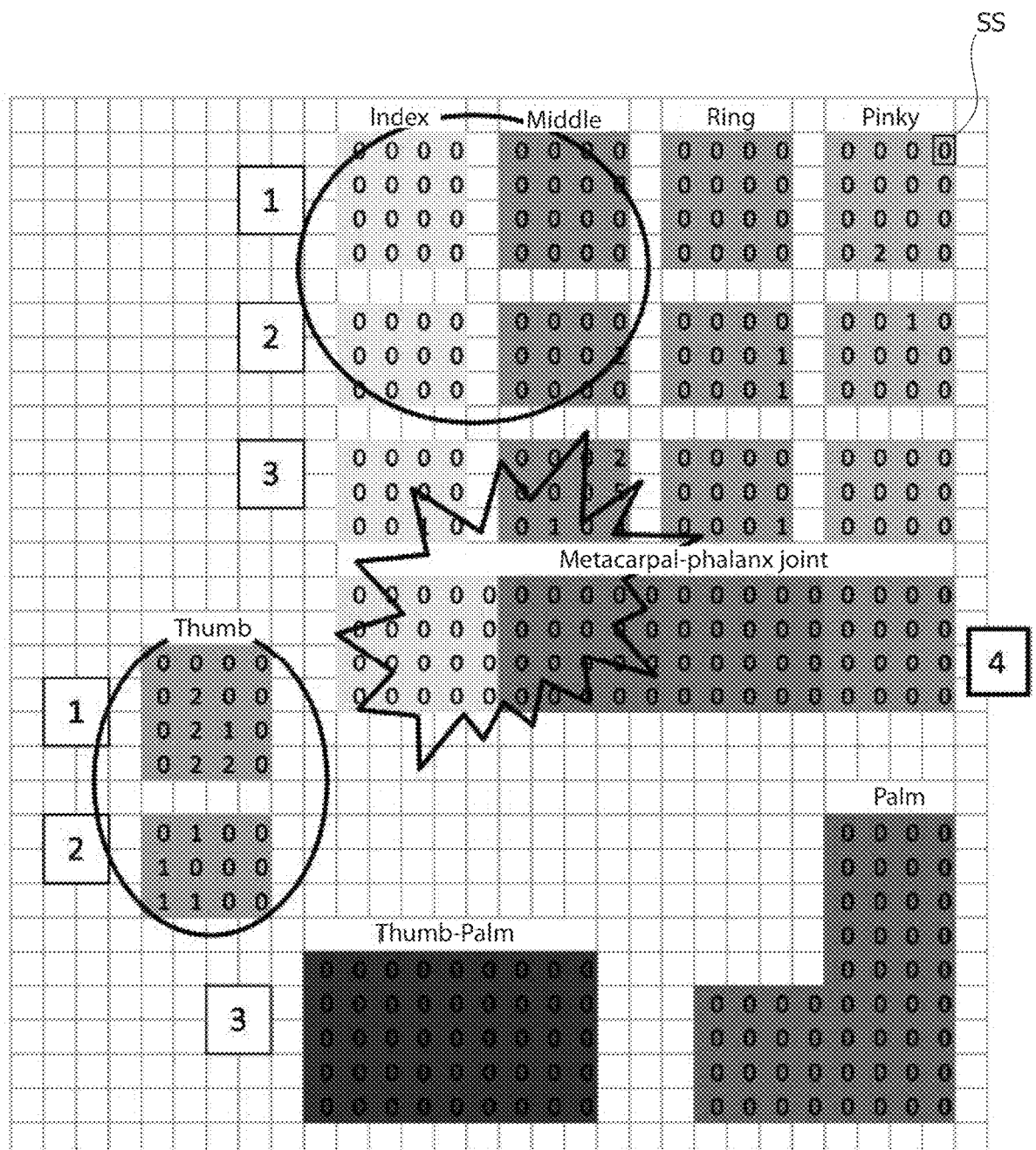

In particular, four different types of grasp may be detected:

a) GRIP: this is the type of grasp exerted, for example, at the moment of gripping an angle nutrunner set in a position corresponding to a joint; for the purposes of the test the results of which appear in FIGS. 9A-9C, the grasp has been made simulating the screwing operation for a duration of 3 s starting from a neutral posture (where by "neutral posture" is meant a hand at rest, i.e., in a posture without any type of grasp and without any load detected by the sensors);

b) PALMAR: this is the type of grasp exerted, for example, at the moment of lifting of a standard weight; for the purposes of the test the results of which appear in FIGS. 10A-10C, a standard weight of 2 kg has been chosen, which (starting from a neutral posture) is picked up from the bench and is lifted, and this posture is held for 3 s, after which the weight is repositioned on the bench;

c) HOOK: this is the type of grasp exerted, for example, at the moment of lifting of a bucket with shaped handle having a known weight; for the purposes of the test the results of which appear in FIGS. 11A-11C, a bucket having a weight of 5.8 kg has been chosen; the bucket is picked up from the ground (starting from a neutral posture) until the point where the arm is fully extended is reached, the posture is held for 3 s, and the bucket is put back on the floor; and d) PINCH: this is the type of grasp exerted, for example, at the moment when a screw is picked up from the working surface; for the purposes of the test the results of which appear in FIGS. 12A-12C, a sequence has been considered that comprises (starting from the neutral posture): picking up a screw from the working surface; positioning the screw on the nut; and manually screwing the screw into the nut with five tightening turns.

To gather information for the purposes of recognition of the types of grasp, calibration tests are conducted on a plurality of operators.

In a case provided by way of example, calibration was carried out on twelve operators according to the following operating scheme:

1) evaluation of the maximum force of each operator in order to assess the ranges of forces; this envisaged the use of instruments such as a gripmeter and a pinchmeter up to the maximum force, with three repetitions;
2) evaluation of the accuracy and precision in acquisition of the force data (deviation from the expected value and the mean value) by gripping the gripmeter with a force of 5 kg kept constant for 3 s, with five repetitions; and
3) evaluation for recognition of the type of grasp (grip/pinch/palmar/hook); a cycle of the four types of grasp was carried out in succession (with neutral posture assumed between each type of grasp), with three repetitions.

Evaluation of the maximum force exerted by each operator both in the case of PINCH (using the pinchmeter) and in the case of GRIP (using the gripmeter)—cf. point 1 above—enables:

evaluation of the range of forces within which the calibration tests and the results thereof (and the results of the future acquisitions in general) are statistically located;

evaluation of the variability of the capacity to exert force between the various subjects of the sample available for each type of grasp; and definition of a minimum threshold value, lower than the maximum force of the weakest operator, to be associated to the reference used in the logic of the software for recognition of the types of grasp.

If in the sample the "weakest" operator is able to exceed the minimum threshold, then there is the reasonable certainty that it is possible to identify a given type of grasp for all the components of the sample; i.e., if the minimum threshold is reached by the weakest subject, certainly the strongest ones will be able to reach and exceed (even abundantly) the activation value. The minimum threshold activates recognition of the type of grasp, filtering any possible background noise or activations of the sensor that are not to be attributed to the type of grasp.

Then, the pressure maps, acquired by the sensors PS were analysed for the various postures of all twelve subjects in order to identify the areas of the hand involved in the various types of grasp.

The values of pressure/force exerted by the various subjects during the various types of grasp were evaluated for assessing the variability of the values due to the subjectivity of execution of the tests.

The results obtained from the pressure maps acquired by the sensors PS have highlighted for the various postures the part involved in the pressures enabling definition of the various types of grasp, meaning thereby that a given configuration of postures and pressures enables (instrumental) identification of a specific type of grasp and hence definition of the reference condition thereof (for the instrument) in order to recognise automatically which type of grasp is being exerted.

Type of Grasp "GRIP"—FIGS. 9A and 9B

The pressure map of FIG. 9A shows a generalised involvement of the entire hand in exerting pressure on the handpiece. With reference to the diagram of FIG. 9B, a certain variability may be noted in the force values detected for the various operators. The diagram of FIG. 9B (this also applies to the subsequent FIGS. 10B, 11B, 12B) represents graphically the plot of the mean force applied on the palm of the hand and detected by the pressure sensors (the topographic map of which may be seen in FIG. 9A, with relative intensity of activation on the basis of the shading). The mean pressures of each sensor multiplied by the area involved in the detection yield a mean force value (F), and the average of the forces (F) detected by the various sensors is the force F represented by the time plot. This is a datum supplied by the instrument for acquisition of the pressures.

Type of Grasp "PALMAR"—FIGS. 10A and 10B

The pressure map of FIG. 10A shows that the areas mostly involved in exertion of pressure are the intermediate and distal phalanges of all five fingers.

The noise on the rest of the hand is generally found to be not higher than 20-30% of the total force exerted by the hand.

With reference to the diagram of FIG. 10B, a certain variability in the force values detected for the various operators may be noted.

Type of Grasp "HOOK"—FIGS. 11A and 11B

The pressure map of FIG. 11A shows that the areas mostly involved in exertion of pressure are the intermediate and distal phalanges of the four fingers and the top part of the palm. The noise on the rest of the hand is not higher than 20% of the total force exerted by the hand.

With reference to the diagram of FIG. 11B, a certain variability may be noted in the force values detected for the various operators.

Type of Grasp "PINCH"—FIGS. 12A and 12B

The pressure map of FIG. 12A shows that the areas mostly involved in exertion of pressure are the intermediate phalanx and the distal phalanx of the thumb, the index finger, and the middle finger. The noise on the rest of the hand is always present, and is in general approximately 30-40% of the total force exerted by the hand.

With reference to the diagram of FIG. 12B, a certain variability may be noted in the force values detected for the various operators.

Logic of Recognition of the Type of Grasp

For each type of grasp, on the basis of the analysis of the previous pressure maps, a given area of the hand on which the majority of the pressure exerted by the hand itself must be concentrated was selected.

For recognition of the type of grasp, the pressures and positions of the areas of the hand involved in the grasp were analysed, and, by way of verification, the pressures and postures of the remaining area of the hand were also analysed. This is illustrated in FIGS. 9C, 10C, 11C, and 12C, where in particular the areas where a measurement of pressure higher than a threshold value is expected to be found are encircled.

Instead, the areas of the pressure map where, for each type of grasp, the concentration of noise (where applicable) is to be expected are encompassed with jagged outlines. The pressure map visible in each figure of this group of figures is arranged as a set of matrices each associated to a sensor PS in a pocket 20, where each cell of each matrix (the so-called sensel, designated by SS) contains the value detected by a sensitive element of the sensor PS in the corresponding area of influence.

GRIP grasp

With reference to FIG. 9C, for the GRIP grasp the pressure must be present over all seventeen areas of the hand. The sensels SS are all concerned in the GRIP grasp, i.e., 361 sensels in the specific example illustrated herein. The total pressure exerted in the case of this type of grasp must be at least 30% higher than the pressure value in the neutral posture. In the majority of cases, the pressure is concentrated in the area of the fingers and in the outer lower area of the palm (L-shaped sensor). The posture of the hand must correspond to the grasp.

PALMAR Grasp

For the PALMAR grasp, the pressure must be concentrated mainly on the intermediate and distal phalanges of all five fingers. There must not be any contact with the area of the palm. The sensels SS concerned for the PALMAR grasp in this specific example are 140 in number (38% of the total area). on this area the pressure must be at least 51% of the total pressure.

On the rest of the hand there may be a residual pressure (noise), which, however, must not exceed 49% of the total pressure. The angles of abduction between the four fingers must be more than 5° to differentiate them from those of the PINCH grasp, and the posture of the hand must correspond to the grasp.

HOOK Grasp

For the HOOK grasp the pressure must be concentrated on the proxIMal and intermediate phalanges of four fingers and on the top part of the palm (pulley). The sensels SS concerned for the HOOK grasp in this specific example are 172 in number (48% of the total area). On this area, the pressure must be at least 51% of the total pressure. There must not be pressure on the thumb; i.e., any possible noise present on the thumb must not exceed the value acquired in the neutral posture. On the rest of the hand (and in particular on the distal phalanges) there may be residual pressure, which, however, must not exceed 49% of the total pressure. The posture of the hand must correspond to the grasp.

PINCH Grasp

For the three-finger PINCH grasp, the pressure must be concentrated mainly on the intermediate and distal phalanges of the thumb, index finger, and middle finger. The sensels SS concerned for the three-finger PINCH grasp in this specific example are 84 in number (23% of the total area). On this area the pressure must be at least 51% of the total pressure. There must always be pressure on the thumb. On the rest of the hand there is frequently a residual pressure (noise), due to bending of the hand, which must not exceed 49% of the total pressure. The angle of abduction between the index finger and the middle finger must be less than 5°. The posture of the hand must correspond to the grasp.

Figure 13:
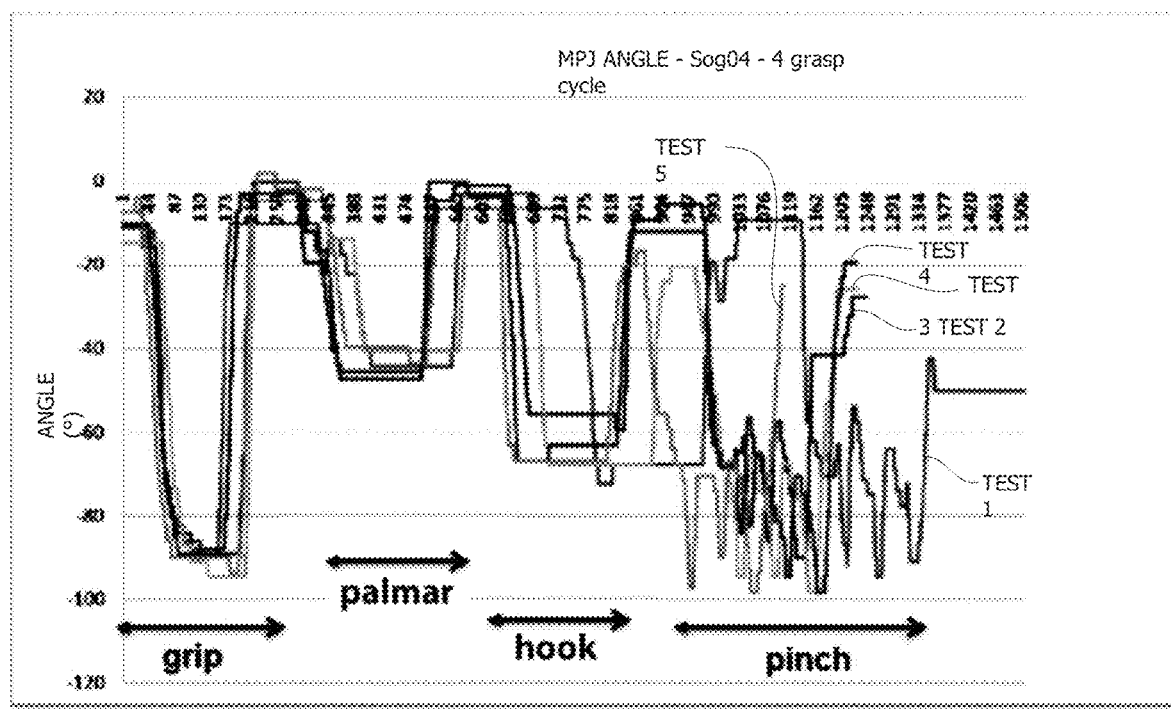
FIG. 13 is a diagram that illustrates four conditions that can be detected using the device of FIG. 2 and the method according to the invention.

The angles that describe the posture of the hand were evaluated during the tests thanks to the data collected via the extensometers EXT on the inner glove 10. A certain repeatability was detected in the angles of the joints of the hand in the various repetitions of the intra-subject test. By way of example, FIG. 13 illustrates the angle acquired for the joint MPJ, which is marked with the same reference as that used in FIG. 3 and corresponds to the point where the middle finger encounters the palm.

In brief, by means of the sensorized glove 2, it is possible to provide a method for ergonomic analysis of a worker's hand that comprises the following steps:

receiving first sensor data from the plurality of extensometer sensors EXT of the inner glove 10;

associating—as described previously—the first sensor data to a vector map of the hand, which comprises a plurality of nodes associated to corresponding joints of the hand, and a plurality of segments that join said nodes to one another, where one or more extensometer sensors EXT associated to a node are configured for detecting a relative angular position between a pair of segments connected to said node, each first sensor datum comprising a relative angular position between the pair of segments connected to the corresponding node;

receiving second sensor data from the plurality of pressure sensors PS of the outer glove 12, each second sensor datum comprising information on the pressure detected along an area of the corresponding pressure sensor PS;

determining, for each pressure sensor PS, a position of a point of application of a resultant force, which is a function of the corresponding second sensor datum, with respect to the nodes (joints J) of said vector map (cf. previous description); and determining, on the basis of the first sensor data in combination with the second sensor data, a type of grasp exerted by the hand.

In particular, the method forming part of the invention, which determines the type of grasp exerted by the hand includes:

defining a pressure map, which comprises a plurality of map areas associated to corresponding pressure sensors PS of the outer glove 12, each map area being an array of sensitive elements SS having a respective area of influence, each sensitive element SS being associated to information representing a pressure value detected on a homologous area of influence on the corresponding pressure sensor PS;

defining involvement thresholds for each map area, where each involvement threshold is defined as a fraction of sensitive elements SS involved over the total number of sensitive elements SS of the map area and is representative of a different type of grasp;

recording the information supplied by the sensitive elements SS of each map area and comparing it with the involvement thresholds that can be applied for the different types of grasp; in this regard, each type of grasp may include a set of involvement thresholds of its own that is descriptive of the situation expected for the grasp in question; and determining the type of grasp on the basis of the outcome of the comparison between the information supplied by the sensitive elements SS of each map area and the involvement thresholds that can be applied for the different types of grasp.

Finally, it should be noted that it is possible to use the first and second sensor data for a cross check on the determination of the type of grasp. In particular, the information determined on the basis of the recording of the information coming from the mapping areas of the pressure map must be consistent with the information determined on the basis of the postural data reconstructed by means of the extensometer sensors EXT of the inner glove 10.

With reference to FIGS. 14 and 15, a wearable sensor network 4 that can be used in a system according to the invention is preferably provided as a sensorized pair of overalls (either in one piece or in two pieces) or an ensemble of wearable accessories 30 (for example, bands, belts, jackets, etc.) that each carry one or more inertial sensors—or sensors in general—designed to provide indications on the postural angles and cartesian co-ordinates in predetermined points of the body. An example of such a wearable network is represented by the sensorized suit produced by Xsens Technologies B.V., P.O. Box 559, 7500 AN ENSCHEDE, The Netherlands.

The sensors that can be installed on the wearable network 4 include, in combination or as alternatives to one another:

accelerometers, for measuring the acceleration in three-dimensional space;

gyroscopes, for measuring the orientation of the Earth's gravity; and/or magnetometers, to have a common reference for the system, i.e., the Earth's magnetic field.

The wearable sensor network 4 envisages that the sensors 30 are located on corresponding parts of the operator's body, where these parts of the operator's body have a correspondence with a reference scheme of the human skeleton illustrated in FIG. 14 and denoted by 4RIF.

The reference scheme 4RIF includes segment elements for defining bones of the human skeleton connected by joint elements for definition of joints of the human skeleton. The joint elements are preferably point-like elements and are identified by the references jC1Head, jT1C7, jT9T8, jL1T12, jL4L3, jL5S1, Root, jRightC7Shoulder, jRightShoulder, jRightElbow, jRightWrist, jLeftC7Shoulder, jLeftShoulder, jLeftElbow, jLeftWrist, jRightHip, jLeftHip, jRightKnee, jRightAnkle, jRightBallFoot, jLeftKnee, jLeftAnkle, jLeftBallFoot. The same references are reproduced also in FIG. 15. Appearing below is a table containing the legend.

| Name of joint | Corresponding anatomic joint |
| --- | --- |
| jC1Head | Head joint - C1 |
| jT1C7 | Sternum joint - T1C7 |
| jT9T8 | Vertebral joint (not sensorised) |
| jL1T12 | Vertebral joint (not sensorised) |
| jL4L3 | Vertebral joint (not sensorised) |
| jL5S1 | Vertebral joint (not sensorised) |
| Root | Vertebral joint (not sensorised) |
| jRightC7Shoulder | Right rear shoulder joint (scapula) |
| jRightShoulder | Right shoulder joint |
| jRightElbow | Right elbow joint |
| jRightWrist | Right wrist joint |
| jRightHip | Right hip joint |
| jRightKnee | Right knee joint |
| jRightBallFoot | Right ball-of-foot joint |
| jRightAnkle | Right ankle joint |
| jLeftC7Shoulder | Left rear shoulder joint (scapula) |
| jLeftShoulder | Left shoulder joint |
| jLeftElbow | Left elbow joint |
| jLeftWrist | Left wrist joint |
| jLeftHip | Left hip joint |
| jLeftKnee | Left knee joint |
| jLeftBallFoot | Left ball-of-foot joint |
| jLeftAnkle | Left ankle joint |

The inertial sensors 30 are arranged in points representative of a respective segment element; in particular, they may be fixed (by means of the aforementioned bands or other type of wearable accessories in general) on respective parts of the body in positions corresponding to points representative of the segment element identified (at a software level) by the joint elements of FIG. 14 that are to be monitored via the network 4.

The network 4 enables acquisition of the kinematics of the body of a person (in the case in point, a worker). In other words, it enables acquisition of the trajectories, postures, angles of rotation that each segment element and joint element of the body assumes during any activity and specifically a working activity. The network 4 is configured for supplying at output values representing a rotation in space (i.e., rotations about the axes x, y, and z) and the spatial co-ordinates for each point monitored.

The above values can be acquired by the processing unit 8, which can automatically evaluate the postures assumed by the worker throughout the working cycle. For instance, it is possible to process the co-ordinates of the joints to obtain angles of rotation of the body joints, in accordance with the indications specified in the ergonomics standards.

The analysis that can be performed by means of the network 4 may be integrated with the analysis conducted on the worker's hands via the glove 2. In general, it is possible to set the network 4 in communication with one or more gloves 2.

The standard distribution of the joints where the postural angles used for the purposes of the ergonomic assessments are detected is represented schematically in FIG. 14. The ergonomically significant angles on which the system according to the invention is designed to act are the following:

angle of the torso;

angle of the shoulder; and angle of the elbow and the knee.

For these angles some definitions and some hypotheses are introduced, namely:

i) vertical line: this is the line between the sagittal plane and the frontal plane;

ii) hip line: this is the line between the points (joints) jRightHip and jLeftHip;

iii) torso line: this is the line between the points (joints) jT1C7 and Root of Xsens;

iv) shoulder line: this is the line between the points (joints) jRightShoulder and jLeftShoulder of Xsens;

v) arm line: this is the line between the points (joints) jRightShoulder and jRightElbow of Xsens;

vi) forearm line: this is the line between the points (joints) jRightElbow and jRightWrist;

vii) thigh line: this is the line between the points (joints) jRightHip and jRightKnee; and viii) leg line: this is the line between the points (joints) jRightKnee and jRightAnkle.

Calculation/Solution for Movements of the Torso

Conditions:

the hip line is aligned to the horizontal and frontal planes;

the flexing angle of the torso is the angle between the vertical line and the torso line projected in the sagittal plane;

the lateral inclination of the torso is the angle between the vertical line and the torso line projected in the frontal plane; and the torsion of the torso is the angle between the shoulder line (measured after the torso is aligned to the vertical line) and the hip line projected in the horizontal plane.

Torso—Forward Bending: Calculation of Reference Geometries

Calculation of Torso Vector $$\overline{P}_{shoulders}=(jRightShoulder+jLeftShoulder)/2 \quad (1)$$

$$\overline{P}_{hips}=(jRightHip+jLeftHip)/2 \quad (2)$$

$$\vec{V}_{torso}=\overline{P}_{shoulders}-\overline{P}_{hips} \quad (3)$$

Calculation of Hip Vector $$\vec{V}_{hips}=jLeftHip-jRightHip \quad (4)$$

Calculation of Sagittal Plane

Initially, the hip vector $\vec{V}_{hips}$ is projected in the horizontal plane, namely, $\vec{V}_{hips}XY=\vec{V}_{hips}$ with the component $\vec{V}_{hips}(z)=0$.

Then, the sagittal plane $\Omega$ is calculated as $$\Omega = (a, b, c) \cdot \begin{cases} x \\ y + d \\ z \end{cases}$$

with:

$$(a,b,c) = \vec{V}_{hips} XY$$

and $$d = \vec{V}_{hips} XY(0) \cdot \vec{P}_{hips}(0) + \vec{V}_{hips} XY(1) \cdot \vec{P}_{hips}(1) + \vec{V}_{hips} XY(2) \cdot \vec{P}_{hips}(2)$$

Application of Method of Solution
Projection of the Torso Vector in the Sagittal Plane
Given the following:
(l, m, n) = $\vec{V}_{torso}$
(a, b, c) = direction coefficients of the sagittal plane $\Omega$ $$k = \left(\frac{1}{n} \cdot c - a\right) \bigg/ \left(b - \frac{m}{n} \cdot c\right)$$

the direction coefficients of the plane $$\Pi = (a_{pi}, b_{pi}, c_{pi}) \cdot \begin{cases} x \\ y + d_{pi} \\ z \end{cases}$$

that contains the straight line passing through $\vec{V}_{torso}$ are calculated as follows:

$$a_{pi} = 1; b_{pi} = k; c_{pi} = -(l + k \cdot m)/n$$

Hence, the projection of the torso vector sought corresponds to the intersection of the two planes $\Pi$ and $\Omega$:

$$\vec{V}_1 = (a_{pi}, b_{pi}, c_{pi}) \times (a, b, c)$$

Vector of Intersection Between Sagittal Plane and Horizontal Plane $$\vec{V}_2 = \vec{V}_{hips} \times (0,0,1)$$

Calculation of Forward Bending as Angle Between $\vec{V}_1$ and $\vec{V}_2$ $$T_F = \cos^{-1}\left(\frac{\vec{V}_1 \cdot \vec{V}_2}{\|\vec{V}_1\| \cdot \|\vec{V}_2\|}\right)$$

The method proposed is independent of the position of the subject with respect to the reference triad of the acquisition system. Moreover, a check on the arccosine enables distinction of the correct sign of the value in the case of flexure (positive sign) and extension (negative sign) of the torso.

Schematic Solution of the Calculation for Forward Bending
 A. Calculation of reference geometries
  i. Calculation of torso vector
  ii. Calculation of hip vector
  iii. Calculation of sagittal plane
 B. Application of method of solution
  i. $V_1$ = projection of the torso vector in the sagittal plane
  ii. $V_2$ = vector of intersection between sagittal plane and horizontal plane
  iii. Calculation of forward bending ($T_F$) as angle between $V_1$ and $V_2$ Calculation/Solution for Movements of the Shoulder
Conditions:
 the shoulder line is aligned to the horizontal and sagittal planes;
 the flexo-extension of the arm is the angle between the vertical line and the arm line projected in the sagittal plane;
 the abduction of the arm is the angle between the vertical line and the arm line projected on the frontal plane;
 if the hand is behind the hip line, there is an extension;
 if the angle between the shoulder line and the arm line, projected in the horizontal plane is less than 45°, there is flexure; otherwise, there is abduction.

Calculation/Solution for Movements of the Elbow and of the Knee
Conditions:
 the flexo-extension of the elbow is the solid angle between the arm line and the forearm line;
 the flexo-extension of the knee is the solid angle between the thigh line and the leg line.

Calculation/Solution for Other Movements
Since the position of the terminal points of the skeleton (top part of the head, end of the hand, end of the foot) is not available, the lateral movements, the flexo-extensions, and the prono-supinations (twisting) of the hands and of the head are calculated on the basis of the information coming from the sensors on the wearable network 4.

The prono-supinations of the hand are instead calculated starting from the rotations of the elbow. Biomechanically, the wrist does not turn: in other words, the hand does not turn with respect to the forearm (using the wrist as hinge). Prono-supination of the hand takes place because, starting from the elbow, there is a rotation of the ulna with respect to the radius; the two long bones are constrained always in the same point both in the wrist and in the elbow but can be cross one another, thus generating prono-supination of the hand. Hence, the prono-supinations of the hand are caused by "rotation" of the long bones starting from the elbow.

The aim of the system 1 according to the invention is the creation of a methodological supporting instrument for ergonomic analysis in the observation and design stage that will at the same time be objective and fast to use.

The development of the methodology of assisted analysis is aimed at a detailed and objective assessment of the activity performed at a workstation, by drawing, from the verification stage, the main factors useful for improving, in the design stage, the product/process parameters on assembly lines.

The general aim is implementation and development of methods for ergonomic assessment of the process in order to apply the data and the information obtained also in the stage of design of new workstations or in the stage of redesign/modification of existing workstations.

For this purpose, the system 1 supplies a simple interface for gathering ergonomic data at input from a working activity, namely, coming from:
 a) the image-acquisition system 6 (FIG. 1C)—avi, mpg files, etc.;
 b) the wearable sensor network 4; and
 c) the sensorized glove 2.

The system 1 is hence able to:
- synchronise the wearable sensor network 4 and the sensorized glove 2, in particular synchronise and jointly use the data supplied thereby;
- integrating and converting the data acquired into ergonomic results;
- identifying the most critical activities of the set of tasks of a worker;
- identifying the main critical aspects from an ergonomic standpoint; and
- supplying an ergonomic assessment in compliance with the international (and company) standards.

The ergonomic methods currently available for the assessments include:
- OCRA Checklist (manual and automatic)
- OCRA Index (manual)
- MURI (manual and automatic)
- EM-MURI (manual)
- RULA (manual)
- Sue Rodgers (manual)
- NIOSH (manual)
- Snook & Ciriello (manual)

In addition to the above, the system enables pre-arrangement of the data for transfer to a specific software for time and ergonomic analysis known as TiCon (automatic).

The features of the system 1 include:
- guided observation of the video clip;
- possibility of data collection and storage according to a clearly defined procedure;
- function of speeding-up of data collection (also automatically by motion-capture systems, such as the network 4 and the glove 2), and organisation of the storage database;
- possibility of analysis of the data (extracted from the video clip) for identification of the ergonomic-risk factors;
- possibility of reprocessing the data observed on the basis of variations of the fundamental ergonomic parameters;
- organisation of data of characterization of localised forces and pressures due to the use of the tools during the working process (dynamic analysis, by means of the sensorized glove 2 and, to a lesser extent, by means of the wearable sensor network 4), and association of the above data to the postures and description of the actions performed (kinematic analysis; in this case the wearable sensor network has at least the same importance as the sensorized glove 2).

The system 1 enables two different methods of data analysis, namely:
- manual analysis (from video); and
- automatic analysis (on the basis of data coming from the network 4 and/or the glove 2); Manual analysis enables execution of an assisted ergonomic analysis starting from one or two synchronised video clips, through:
- identification of the critical postures by pressing the specific keys of the keypad while the video clip is being run; and
- automatic calculation of the times and of the ergonomic indices required.

Automatic analysis enables reading of the data at output from the wearable sensor network 4 and the glove 2 (which records the movements of the user) for automatic recognition of the majority of the critical postures.

The above analysis has been implemented prevalently for some ergonomic methods (OCRA Checklist and MURI); moreover, in this way, some input data are also available for the TiCon© software.

For operation of the system 1 in manual mode, it is indispensable to acquire at least one video clip of the workstation that is to be analysed. If the video clip is the only kind of data that is acquired, then only a manual analysis is possible. If, instead, acquisition of the video clip is combined with acquisition of the data from the wearable network 4 and/or from the sensorized glove 2, then it is possible to carry out an automatic analysis.

The software has two interfacing modes:
a) "input mode", where the software autonomously activates the manual mode or automatic mode according to the files loaded; in the case of activation in manual mode it is possible to select the ergonomic items that are to be implemented manually; and
b) "output mode", where visible (on a screen) is the distribution in time of the characteristics entered manually or calculated starting from the data-acquisition files of the network 4 and the glove 2.

Operating Logic of the System According to the Invention

The system 1 according to the invention is preferably entirely implemented and managed via software. The premises for ergonomic analysis are the availability of at least one video clip of the working activity that is to be analysed, or else (either in combination or as an alternative) an IVR (Immersive Virtual Reality) system.

The second option is implemented in particular in the design stage when the physical workstation for the operator does not yet exist, and envisages integration of the glove 2 and of the wearable network 4 with the IVR system in combination with the use of real tools and objects, such as wrenches, screwdrivers, and line structures in a context commonly identified as "mixed reality". To be able to pursue this option, it is necessary to have available a CAD model of the workstation that is to be analysed, and it is likewise necessary to know the working cycle of the task to be performed.

The software whereby operation of the system 1 is implemented is configured for reading the majority of the commercially available types of video files. In the case of manual analysis, it is possible to proceed with post-processing analysis of the various ergonomic items that are to be assessed.

In the case of operation in IVR mode, instead of the availability of the video clip of the operator working at the workstation, a video file is provided, obtained following upon implementation of the following operating logic:
- importation into the virtual environment of the CAD model of the workstation to be analysed;
- definition of the logic of movement of the tools (wrench, screwdriver, etc.) to be used in the virtual environment;
- assignment of the real object to the corresponding virtual object;
- preparation of the user who will be wearing both the network 4 and the glove 2; and
- reproduction of the work task and recording of the data.

In this way, it is possible to generate a video file (for example, in.mpg format) to be used instead of the video clip captured on-line at the real workstation, integrating it with the data recorded by the network 4 and the glove 2.

In this regard, reference may be made to FIGS. 20 and 21, which illustrate, in the portion A, a user U equipped with the wearable network 4, a pair of gloves 2 (a right-hand one and a left-hand one), and a pair of VSR glasses.

FIG. 20 shows the user U, who is interacting with a structure F that represents a resting surface available in the physical workstation so that the user is supported in the posture as in the real working environment. FIG. 20B illustrates the virtual transposition of the condition of the user U in FIG. 20A, which on the other hand corresponds to the display available to the user through the VSR glasses.

FIG. 21 shows, instead, the user U who is handling a real tool T, for example, a screwdriver. FIG. 21B illustrates the virtual transposition of the condition of the user U in FIG. 20A, which on the other hand corresponds to the display available to the user through the VSR glasses.

It should be noted that the use of physical elements such as the structure F or the screwdriver T in the IVR system is preferable in order to prevent erroneous interpretations of the postural data and, above all, of the grasp data.

At the start, the software is set in INPUT mode. In this mode, the processing unit 8 automatically acquires the data coming from the wearable sensor network 4 and/or from the sensorized glove 2, or else receives the input data via manual data entry. In this mode, it is possible to select the ergonomic method that is to be used for the assessment.

Figure 16:
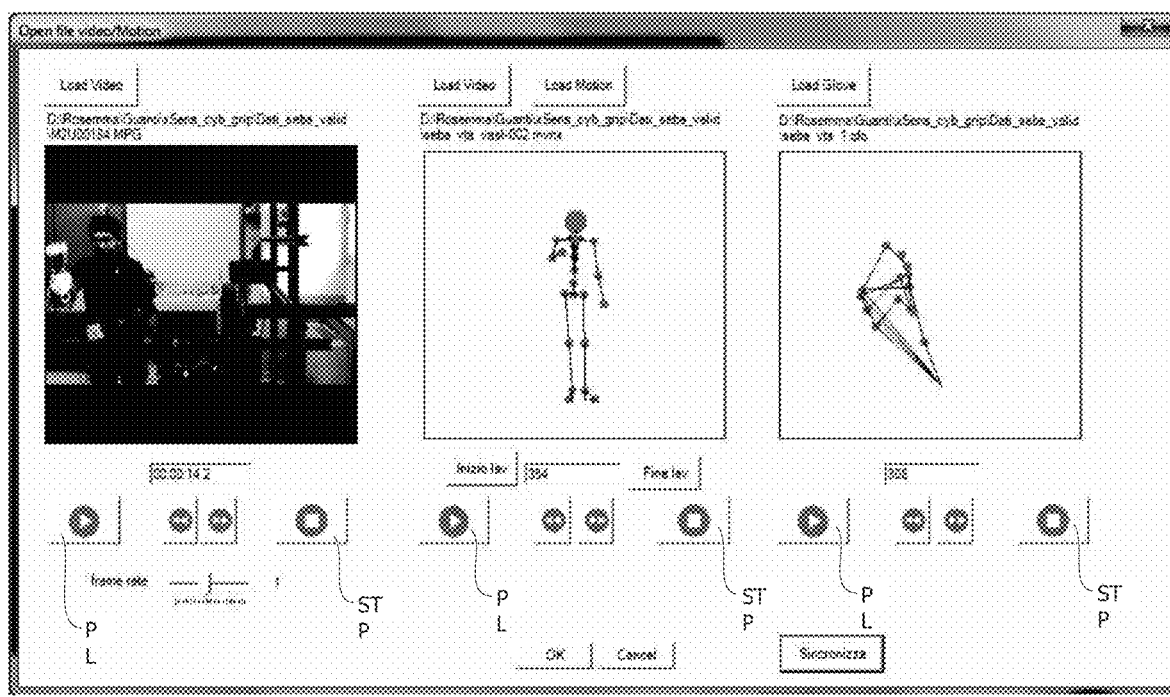

Represented in FIG. 16 is an interface that enables simultaneous opening of a video clip acquired by the one or more image-acquisition devices 6 and/or a video clip generated by means of the IVR system, a reconstruction of the posture of the body of the worker obtained by means of the data coming from the network 4, and/or a reconstruction of the posture of the hands that can be obtained by processing the data received from the sensorized glove 2.

Once the video and animation files of the software dummy have been opened (the software dummy being represented in the central image of FIG. 16 and corresponding to a human model generated in software environment and managed in software environment; operatively, it is the model of the human skeleton associated to the sensor network), access is gained to the interface that enables representation of an analysis of some movements simultaneously with display, for example, of actions, pressures/forces, or types of grasp of the hands, that may be considered important for the purposes of ergonomic analysis.

OCRA Checklist Method

The OCRA (Occupational Repetitive Actions) Checklist method consists, as is known, of a synthetic index for assessment of the work risk factors affecting musculo-skeletal disorders of the upper limbs that is able to identify the risk of overload of the upper limbs due to repetitive work.

If the data of the network 4 are available (i.e., in the case where the data files acquired by means of the device are available), the following characteristics already calculated are automatically available:

i) arm almost at shoulder height;
ii) hand above the head;
iii) extreme prono-supinations of the elbow;
iv) extreme flexo-extensions and deviations of the wrist;

If data acquired by the sensorized glove 2 are also available, also the following further characteristics are automatically available (according to the methodologies already described previously):

v) recognition of the various types of grasp, with notification of the presence of an incongruous grasp (pinch grasp, palmar grasp, or hook grasp: in this connection, these types of grasp can cause biomechanical overloads if they are repeated frequently or even damage due to squeezing of the sinovial capsules of the tendons of the hand; hence they must be detected and, if they are carried out frequently, they contribute to raising the ergonomic-risk index); and vi) recognition of the static actions.

The ergonomic items that are not analysed automatically may be analysed manually by the user. An example of graphic interface that can be used for this purpose is illustrated in FIG. 17, portion A.

The ergonomic items may be selected in a menu "ITEM" that appears on the right of the screen. In this embodiment, it is possible to analyse up to a maximum of four ergonomic items at a time, but it is possible to carry out the analysis also by selecting just one item at a time.

In the case where a data file generated by acquisition by the network 4 has been selected, after entry of an enable command by the user (for example, by pressing a button "play" or "start", see reference PL in FIG. 17; the reference STP identifies, instead, a stop key), automatically the software calculates the ergonomic information of the OCRA Checklist method for the items mentioned previously.

If, instead, no motion-capture files coming from the network 4 and/or from the glove 2 are available, it is possible to proceed with manual analysis as follows (FIGS. 17A and 17B) by:

1. pressing the key PL to run the video clip or continue display thereof; by pressing the key PL again the video clip is paused;

2. pressing, on a keypad KYP, the character or characters corresponding to the ergonomic item that is being analysed in the instants of the video in which the item is present; in the example in the figure, the representative characters are "A", "S", "K", and "L";

3. once acquisition of all the necessary ergonomic items is through, displaying and checking again, if so required, the acquisition just concluded, and then passing to the output step.

Using a mode-selection menu, it is then possible to pass to the OUTPUT mode, thus displaying the results for the data entered.

Figure 18:
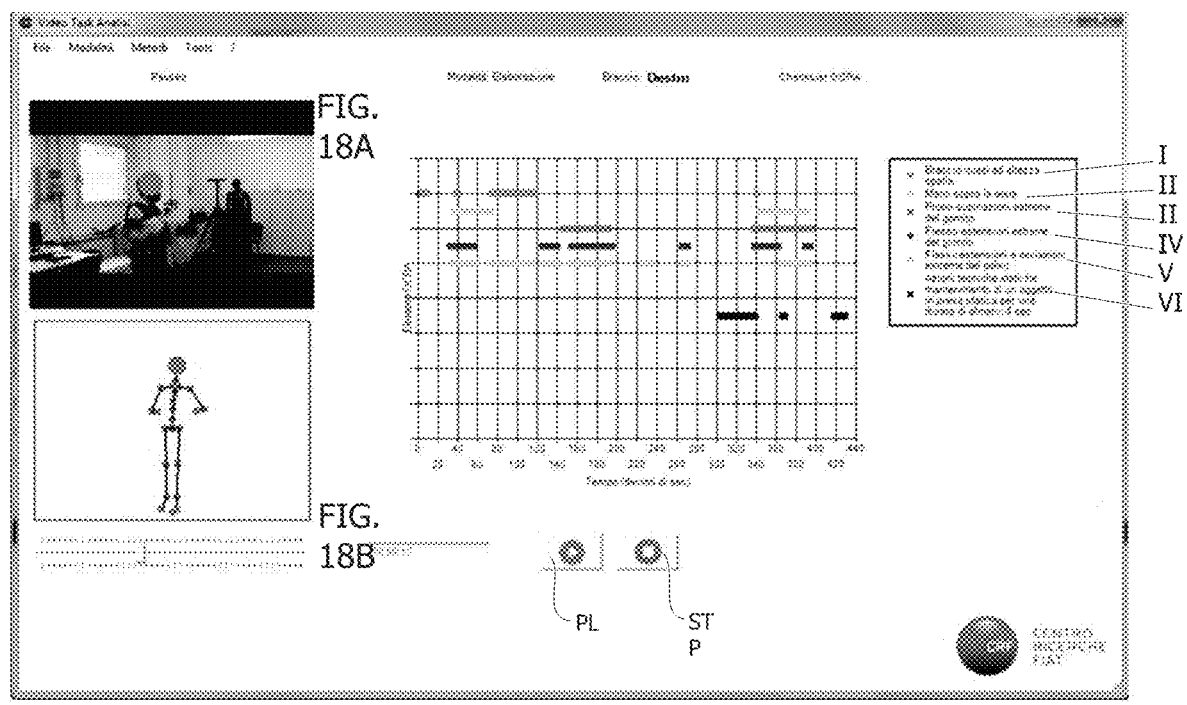

An example of screen containing results is illustrated in FIG. 18: a graph is displayed, which shows the presence and temporal distribution of the items in the task analysed. In particular, in the case in point, all the items of points i) to iv) and vi) above are displayed, i.e., i) arm almost at shoulder height;
ii) hand above the head;
iii) extreme prono-supinations of the elbow;
iv) extreme flexo-extensions and deviations of the wrist;
vi) static technical actions: holding an object in static grasp for at least 4 s.

In the case where also the data of the glove 2 were collected, to the items in question there would be added the item of point v) above, i.e., recognition of the various types of grasp and of incongruous grasps.

By querying on the graph a point where an ergonomic item is present (for example, by clicking the point with the mouse), it is possible to display the corresponding instant of the video clip where said item occurs. In the case of acquisition of the motion-capture data by the network 4, the corresponding posture of the equivalent dummy is reproduced (FIG. 18B).

Once acquisition is through, it is moreover possible to check again the times calculated on the basis of the OCRA Checklist method, i.e., the times associated to occurrence and protraction of the various items.

The data may moreover be exported in a high-compatibility format for external analyses, for example in a Microsoft® Excel® spreadsheet.

OCRA Index Method

A second ergonomic method is the OCRA Index method, based upon the ISO 11228-3 standards, which may enable further movements of the body to be evaluated, for example: rotation of some joints through an angle that exceeds predetermined thresholds. Via this analysis, it is possible to obtain an evaluation of an index of risk for the worker.

The operating modes of data acquisition and assessment of the ergonomic items are the same as those already described.

MURI and EM-MURI Methods

A further ergonomic method is the MURI method, whereby it is possible to divide the time interval observed into a number of study periods so as to obtain a division of the actions performed by a worker, for example analysed automatically and simultaneously. At the end of the assessment, it is possible to obtain a number of evaluations of the actions performed by a worker, instead of a single evaluation of the ergonomic analysis (i.e., based upon a single ergonomic-risk index).

In combination with other ergonomic methods, also the EM-MURI ergonomic method may be used, which consists in an extended version of the MURI analysis (i.e., with more parameters evaluated). The purpose of this method is to enable a rapid assessment of the ergonomic risks and to overestimate certain ergonomic risks in such a way as to highlight the actions on which it may be interesting to conduct a subsequent analysis.

After reading the video file corresponding to the video acquired by means of the device 6 and, if available, also the motion-capture file acquired with the network 4, the various periods into which the task to be analysed is to be divided are defined.

As the video clip is run, the key PL (play/pause) can be used to pause the video clip at the final instant of the study period forming part of the set of periods into which the task is to be divided, and the study period is identified by pressing a dedicated key; this operation is repeated until all the study periods have been considered.

The time of start and end of the period selected are recorded automatically by the software that calculates duration thereof, starting from the (start/end) data entered manually.

In the case where data of the network 4 are available, the ergonomic items that do not refer to loads to be moved will be analysed automatically by the software. The reason for this is that in the MURI method one datum that cannot be collected using the sensors described is the load (weight) to be moved or carried so that this datum must be entered manually. The remaining data necessary for assessment can arrive automatically from the sensors.

In the case where only the video clip is available, after all the periods that identify the task to be analysed have been entered, it is necessary to select the ergonomic item that is to be analysed. The video clip is then restarted, and the period corresponding to that item is automatically highlighted and selected.

While a period is highlighted, the operator who carries out the analysis must type in a vote that he intends to attribute to the corresponding ergonomic item in the period in question. The voting system envisages the following scale: 1 acceptable; 2 investigate; 3 unacceptable; these votes may possibly be associated to colours (e.g., green=acceptable; yellow=investigate; red=unacceptable).

Figure 19:
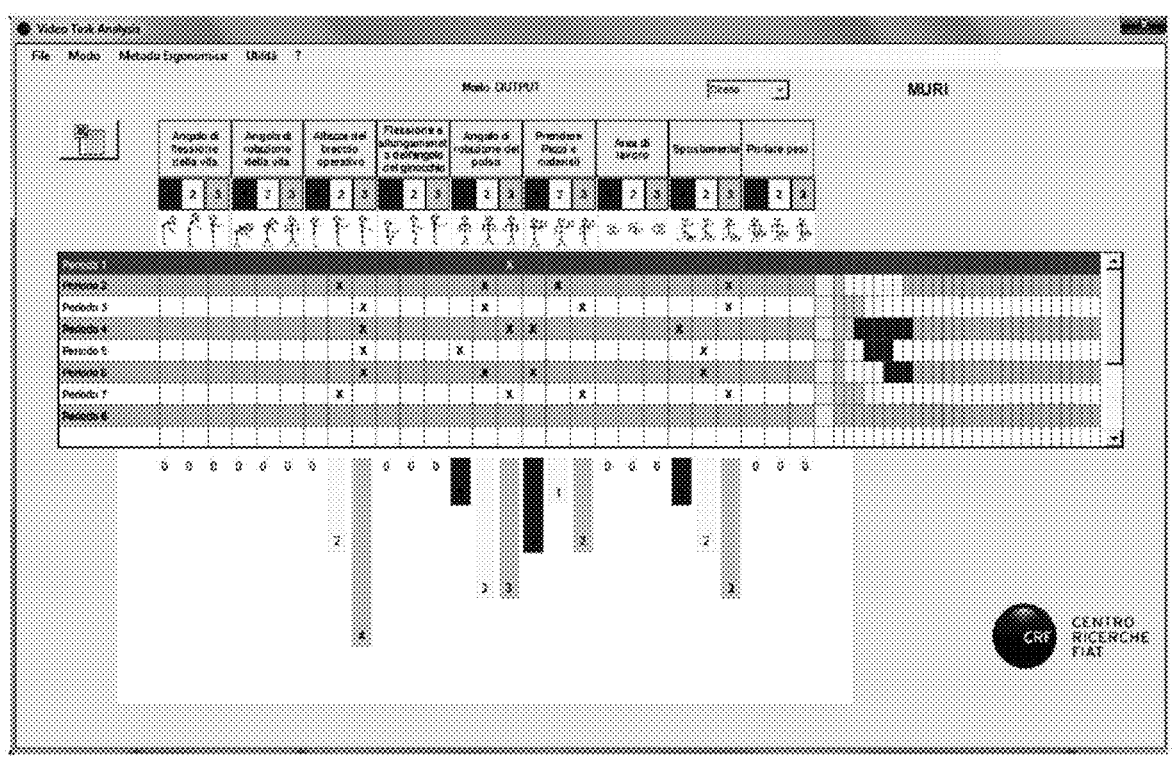

In the output mode, a graph is displayed summarising the MURI data divided into periods/operations that have been analysed. An example of this graph is displayed in FIG. 19.

TiCon Method and Software

Yet a further ergonomic method corresponds to the EAWS method and corresponding TiCon software for ergo-characterization, i.e., for the activity of definition of the ergonomic parameters that distinguish from the ergonomic standpoint an activity (described in the acquisition of times or operation) on the basis of the workstation to which said activity has been assigned (balancing).

The analysis via the EAWS method is performed with the TiCon software, which may advantageously be fed with the data drawn from the system 1 since it enables, for example, assessment of:

the type of grasp of a hand;

the angles at which the wrist is turned; and a height at which an operation is carried out, and a distance, direction, and force with which the body performs an operation.

Further Ergonomic Methods that Draw Benefit from the Analysis Conducted Using the System 1

RULA (Rapid Upper-Limb Assessment) ergonomic method: this method is used for assessing musculo-skeletal risks due to incongruous postures maintained in a continuous or repetitive way during working activity.

NIOSH (National Institute for Occupational Safety and Health) ergonomic method: this method may be used for assessing the risk involved in lifting loads.

Snook & Ciriello ergonomic method: this method is used for assessing a risk correlated to transporting on the flat, pulling, or pushing a load.

Sue Rodgers ergonomic method: this method is used for analysis of muscle fatigue, in particular in the Brazilian industry.

Irrespective of the ergonomic method that is chosen for the ergonomic analysis via the system 1, the general steps listed below of the method for ergonomic analysis of a worker using the system 1 can thus be identified.

These steps comprise:

acquiring a sequence of images of a task of the worker by means of the unit for generation of a sequence of images (6); this may comprise, in combination or as an alternative to one another: acquiring a video clip of the operator at the workstation; and/or generating a video clip via interaction of a reference operator (the user U) with a virtual workstation (e.g., the CAD model of the workstation) in a virtual-reality system, in particular and immersive-virtual-reality system;

acquiring a first set of postural data from the sensorized glove 2; this corresponds to the steps and to the method already described previously in relation to determination of posture and types of grasp of the hand using the glove 2;

acquiring a second set of postural data from the wearable sensor network 4; and determining one or more ergonomic indicators on the basis of the first set of data, the second set of data, and the sequence of images.

Acquiring a second set of postural data from the wearable sensor network 4 comprises acquiring the trajectories, postures, and angles of rotation of each segment element and joint element of said reference scheme during performance of the task.

By means of the above method and using the system 1 it is hence in general possible to identify aspects that are critical from an ergonomic standpoint, and/or to provide an ergonomic assessment in compliance with company and international standards, and/or to re-plan a workstation or a sequence of operations to reduce the ergonomic risk to which the operator is exposed.

Of course, the details of implementation and the embodiments may vary widely with respect to what has been described and illustrated herein, without thereby departing from the sphere of protection of the present invention, as defined by the annexed claims.

The invention claimed is:

1. A system for ergonomic analysis including:
   a sensorized glove, said sensorized glove comprising an inner glove, which includes a plurality of extensometer sensors configured for detecting relative movements between parts of a worker's hand of a human body, and
   an outer glove, which includes a plurality of pressure sensors distributed over an outer glove palmar surface and configured for detecting pressure exerted in corresponding areas of said outer glove palmar surface;
   a wearable network of sensors being located in a network so that they can be associated to corresponding joints of the human body;
   a system for generating a sequence of images of a task performed by the worker; and
   a processing unit configured for receiving data and/or signals from the sensorized glove, and/or from the wearable network of sensors, and/or from the system for generating a sequence of images, and configured for processing said data and/or signals in order to estimate ergonomic indicators, and/or to obtain local information of effort and/or posture.

2. The system according to claim 1, wherein said system for generating a sequence of images comprises one or more cameras configured for acquisition of a video of the worker within a working area.

3. The system according to claim 1, wherein said system for generating a sequence of images comprises an Immersive Virtual Reality system where an environment corresponds to a CAD model of a workstation of the worker.

4. The system according to claim 1, wherein in said sensorized glove said inner glove includes an inner glove dorsal surface and an inner glove palmar surface, and comprises:
   a first plurality of pockets, housed within which are corresponding linear extensometers; and
   a second plurality of pockets, which are substantially U-shaped and house corresponding linear extensometers configured for detecting relative movements of parts of the hand in a palmar plane.

5. The system according to claim 4, wherein said outer glove includes an outer glove dorsal surface and the outer glove palmar surface and comprises a third plurality of pockets on said outer glove palmar surface configured for housing a corresponding pressure sensor.

6. The system according to claim 1, wherein each pressure sensor is part of a pressure sensor network with a layout such as to enable application of individual sensors in predetermined areas of the hand.

7. The system (1) according to claim 1, wherein said plurality of extensometer sensors and said plurality of pressure sensors have at least partially overlapping areas.

8. A method for ergonomic analysis of a worker by the system according to claim 1, comprising:
   acquiring a sequence of images of a task performed by the worker by said system for generating the sequence of images;
   acquiring a first set of postural data from said sensorized glove;
   acquiring a second set of postural data from said wearable sensor network; and
   determining one or more ergonomic indicators on a basis of said first set of data, said second set of data, and said sequence of images.

9. The method according to claim 8, wherein acquiring a first set of postural data from said sensorized glove comprises:
   receiving first sensor data from said plurality of extensometer sensors of said inner glove;
   associating said first sensor data to a vector map of the hand, which comprises a plurality of nodes associated to corresponding joints of the hand, and a plurality of segments that join said nodes to one another, wherein one or more extensometer sensors associated to a node of the plurality of nodes are configured for detecting a relative angular position between a pair of segments connected to said node, each first sensor datum comprising a relative angular position between the pair of segments connected to the corresponding node;
   receiving second sensor data from said plurality of pressure sensors of said outer glove, each second sensor datum comprising information of pressure detected along an area of the corresponding pressure sensor;
   determining, for each pressure sensor of said outer glove, a position of a point of application of a resultant force, which is a function of the corresponding second sensor datum, with respect to the nodes of said vector map; and
   determining, on the basis of the first sensor data in combination with the second sensor data, a type of grasp exerted by the hand.

10. The method according to claim 9, wherein said determination of a type of grasp exerted by the hand includes:
    defining a pressure map, which comprises a plurality of map areas associated to corresponding pressure sensors of said outer glove, each map area being an array of sensitive elements having a respective area of influence, each sensitive element being associated to information representing a pressure value detected on a homologous area of influence on the corresponding pressure sensor;
    defining involvement thresholds for each map area, wherein each involvement threshold is representative of a different type of grasp;
    recording the information supplied by the sensitive elements of each map area and comparing it with the involvement thresholds that can be applied for the different types of grasp; and
    determining the type of grasp on a basis of an outcome of the comparison between the information supplied by the sensitive elements of each map area and the involvement thresholds that can be applied for the different types of grasp.

11. The method according to claim 10, further including carrying out a check on the determination of the type of grasp by comparing the type of grasp determined with postural information determined on a basis of said first sensor data.

12. The method according to claim 8, wherein said wearable sensor network comprises inertial sensors located on corresponding parts of the body of the worker, said parts of the body of the worker having a correspondence with a reference scheme of a human skeleton, said reference scheme including segment elements for definition of bones of the human skeleton connected by joint elements for definition of joints of the human skeleton, the inertial sensors being arranged in points representative of a respective segment element.

13. The method according to claim 12, wherein acquiring a second set of postural data from said wearable sensor network comprises acquiring the trajectories, postures, and angles of rotation of each segment element and joint element of said reference scheme during performance of the task.

14. The method according to claim 12, wherein the joint elements are point-like elements.

15. The method according to claim 8, wherein acquiring a sequence of images comprises, in combination or as an alternative to one another:

acquiring a video of the worker at a workstation; and
generating a video by interaction of a reference worker with a virtual workstation in a virtual-reality system.

* * * * *